United States Patent
Lu et al.

(10) Patent No.: US 8,258,099 B2
(45) Date of Patent: Sep. 4, 2012

(54) PIN1-MODULATING COMPOUNDS AND METHODS OF USE THEREOF

(75) Inventors: Kun Ping Lu, Newton, MA (US);
Robert K. Suto, Shrewsbury, MA (US);
Janusz M. Sowadski, Boston, MA (US);
Gunter S. Fischer, Halle (DE); Joseph P. Noel, San Diego, CA (US); Mark Verdecia, Ozone Park, NY (US)

(73) Assignees: Max-Planck-Gesellschaft zur Foerderung der Wissenschaften E.V., Munich (DE); Beth Israel Deaconess Medical Center, Inc., Boston, MA (US); The Salk Institute for Biological Studies, La Jolla, CA (US)

( * ) Notice: Subject to any disclaimer, the term of this patent is extended or adjusted under 35 U.S.C. 154(b) by 1151 days.

(21) Appl. No.: 11/632,588

(22) PCT Filed: Jul. 15, 2005

(86) PCT No.: PCT/US2005/025097
§ 371 (c)(1),
(2), (4) Date: Dec. 28, 2007

(87) PCT Pub. No.: WO2006/019982
PCT Pub. Date: Feb. 23, 2006

(65) Prior Publication Data
US 2008/0214470 A1    Sep. 4, 2008

Related U.S. Application Data

(60) Provisional application No. 60/588,421, filed on Jul. 15, 2004.

(51) Int. Cl.
*C07K 7/00* (2006.01)
(52) U.S. Cl. .................................. 514/19.3; 530/332
(58) Field of Classification Search .................... None
See application file for complete search history.

(56) References Cited

U.S. PATENT DOCUMENTS

| | | | |
|---|---|---|---|
| 5,753,617 A | 5/1998 | Heavner et al. | |
| 6,329,499 B1 | 12/2001 | Ling et al. | |
| 2002/0025521 A1 | 2/2002 | Lu et al. | |

OTHER PUBLICATIONS

Zhang et al Biochemistry vol. 41 p. 11868 (2002).*

* cited by examiner

*Primary Examiner* — Sheela J Huff
(74) *Attorney, Agent, or Firm* — Kristina Bieker-Brady; Clark & Elbing LLP

(57) ABSTRACT

The invention is directed to peptide modulators of Pin1 and Pin1-related proteins and the use of such modulators for treatment of Pin1 associated states, e.g., for the treatment of cancer or neurodegenerative disease.

28 Claims, 12 Drawing Sheets

A

B

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term acetylation
<220> FEATURE:
<221> NAME/KEY: MOD_RES
<222> LOCATION: (1)..(1)
<223> OTHER INFORMATION: Lys(N-epsilon-biotinoyl)
<220> FEATURE:
<221> NAME/KEY: MOD_RES
<222> LOCATION: (4)..(4)
<223> OTHER INFORMATION: Bth (benzothiophene)
<220> FEATURE:
<221> NAME/KEY: MOD_RES
<222> LOCATION: (5)..(5)
```

```
<223> OTHER INFORMATION: Thr(PO3H2)
<220> FEATURE:
<221> NAME/KEY: MOD_RES
<222> LOCATION: (6)..(6)
<223> OTHER INFORMATION: Pip
<220> FEATURE:
<221> NAME/KEY: MOD_RES
<222> LOCATION: (7)..(7)
<223> OTHER INFORMATION: Nal
<220> FEATURE:
<223> OTHER INFORMATION: C-term amidation

<400> SEQUENCE: 1

Lys Ala Ala Xaa Thr Xaa Ala Gln
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: H-Abz
<220> FEATURE:
<223> OTHER INFORMATION: C-term -NH-Np

<400> SEQUENCE: 2

Xaa Ala Glu Pro Phe
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Suc-Ala
<220> FEATURE:
<223> OTHER INFORMATION: C-term -NH-Np

<400> SEQUENCE: 3

Ala Arg Pro Phe
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term acetylation
<220> FEATURE:
<221> NAME/KEY: MOD_RES
<222> LOCATION: (3)..(3)
<223> OTHER INFORMATION: Ser(PO3H2)
<220> FEATURE:
<223> OTHER INFORMATION: C-term -NH-Np

<400> SEQUENCE: 4

Ala Ala Ser Pro Arg
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term acetylation
<220> FEATURE:
<221> NAME/KEY: MOD_RES
<222> LOCATION: (2)..(2)
<223> OTHER INFORMATION: L-Thr(PO3H2)
<220> FEATURE:
<221> NAME/KEY: MOD_RES
<222> LOCATION: (3)..(3)
<223> OTHER INFORMATION: Pip
<220> FEATURE:
<221> NAME/KEY: MOD_RES
<222> LOCATION: (4)..(4)
<223> OTHER INFORMATION: Nal
<220> FEATURE:
<223> OTHER INFORMATION: C-term amidation

<400> SEQUENCE: 5

Phe Thr Xaa Ala Gln
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term acetylation
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Thr(PO3H2)
<220> FEATURE:
<221> NAME/KEY: MOD_RES
<222> LOCATION: (3)..(4)
<223> OTHER INFORMATION: Any amino acid
<220> FEATURE:
<223> OTHER INFORMATION: C-term -NHCH((CH2)2CONH-linker)COOH

<400> SEQUENCE: 6

Xaa Thr Xaa Xaa
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Suc-Ala
<220> FEATURE:
<223> OTHER INFORMATION: C-term -NH-Np

<400> SEQUENCE: 7

Ala Ala Pro Phe
1
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term acetylation
<220> FEATURE:
<221> NAME/KEY: MOD_RES
<222> LOCATION: (1)..(1)
<223> OTHER INFORMATION: Lys(N-epsilon-biotinoyl)
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Thr(PO3H2)
<220> FEATURE:
<221> NAME/KEY: MOD_RES
<222> LOCATION: (6)..(7)
<223> OTHER INFORMATION: Any amino acid
<220> FEATURE:
<223> OTHER INFORMATION: C-term amidation

<400> SEQUENCE: 8

Lys Ala Ala Xaa Thr Xaa Xaa Gln
1               5
```

PIN1-MODULATING COMPOUNDS AND METHODS OF USE THEREOF

RELATED APPLICATIONS

This application is the U.S. National Stage of International Application No. PCT/US2005/025097, filed on Jul. 15, 2005, which claims the benefit of and priority to U.S. Provisional Application No. 60/588,421, filed Jul. 15, 2004, the entire contents of which are incorporated herein by reference.

BACKGROUND OF THE INVENTION

The peptidyl-prolyl cis-trans isomerases (PPIases), or rotamases, are a family of ubiquitous enzymes that catalyze the cis/trans isomerization of the peptide bond on the N-terminal side of proline residues in proteins (Hunter, Cell 92:141-142, 1998). PPIases are divided into three classes, cyclophilins (Cyps), FK-506 binding proteins (FKBPs) and the Pin1/parvulin class.

Cyclophilins and FKBPs are distinguished by their ability to bind the clinically immunosuppressive drugs cyclosporin and FK506, respectively (Schreiber, Science 251:283-7, 1991; Hunter, supra). Upon binding of these drugs, there are two common outcomes: inhibition of the PPIase activity and inhibition of the common target calcineurin. The inhibition of calcineurin phosphatase activity prevents lymphocytes from responding to antigen-induced mitogenic signals, thus resulting in immunusuppression. However, the inhibition of the PPIase activity is apparently unrelated to the immunosuppressive property of the drug/PPIase complexes. Even more surprisingly, deletion of all 8 known cyclophilins and 4 FKBPs in the same cells does not result in any significant phenotype (Dolinski et al., Proc. Natl. Acad. Sci. USA 94:13093-131098, 1997).

In contrast, members of the Pin1/parvulin class of PPIases bind neither of these immunosuppressive drugs, and are structurally unrelated to the other two classes of PPIases. Known members of the Pin1/parvulin class include Pins1-3 (Lu et al., Nature 380; 544-547, 1996), Pin-L (Campbell et al., Genomics 44:157-162, 1997), parvulin (Rahfeld, et al., Proc. Natl. Acad. Sci. USA 93:447-451, 1996) and Ess1/Pft1 (Hanes et al., Yeast 5:55-72, 1989; and Hani, et al. FEBS Letts 365:198-202, 1995).

Pin1 (Accession number: AAC50492) is a highly conserved protein that catalyzes the isomerization of only phosphorylated Ser/Thr-Pro bonds (Rananathan, R. et al. 1997 Cell 89:875-86; Yaffe, et al. 1997, Science 278:1957-1960; Shen, et al. 1998, Genes Dev. 12:706-720; Lu, et al. 1999, Science 283:1325-1328; Crenshaw, et al. 1998, Embo J. 17:1315-1327; Lu, et al. 1999, Nature 399:784-788; Zhou, et al. 1999, Cell Mol. Life. Sci. 56:788-806). In addition, Pin1 contains an N-terminal WW domain, which functions as a phosphorylated Ser/Thre-Pro binding module (Sudol, M. (1996) Prog. Biophys. Mol. Biol. 65:113-32). This phosphorylation-dependent interaction targets Pin1 to a subset of phosphorylated substrates, including Cdc25, Wee 1, Myt1, Tau-Rad4, and the C-terminal domain of RNA polymerase II large domain (Crenshaw, D. G., et al. (1998) Embo. J. 17:1315-27; Shen, M. (1998) Genes Dev. 12:706-20; Wells, N. J. (1999) J. Cell. Sci. 112: 3861-71).

The specificity of Pin1 activity is essential for cell growth; depletion or mutations of Pin1 cause growth arrest, affect cell cycle checkpoints and induce premature mitotic entry, mitotic arrest and apoptosis in human tumor cells, yeast or *Xenopus* extracts (Lu, et al. 1996, Nature 380:544-547; Winkler, et al. 2000, Science 287:1644-1647; Hani, et al. 1999. J. Biol. Chem. 274:108-116). In addition, Pin1 is dramatically misregulated in human cancer samples. Moreover, inhibition of Pin1 by various approaches, including Pin1 antisense polynucleotides or genetic depletion, kills human and yeast dividing cells by inducing premature mitotic entry and apoptosis. Further, Pin1 has been shown to be involved with the progression of neurodegenerative diseases such as Alzheimer's' disease.

Thus, Pin1-catalyzed prolyl isomerization regulates the conformation and function of these phosphoprotein substrates and facilitates dephosphorylation because of the conformational specificity of some phosphatases. Thus, Pin1-dependent peptide bond isomerization is a critical post-phosphorylation regulatory mechanism, allowing cells to turn phosphoprotein function on or off with high efficiency and specificity during temporally regulated events, including the cell cycle (Lu et al., supra).

SUMMARY OF THE INVENTION

A need exists for new diagnostic and therapeutic compounds for diseases characterized by uncontrolled cell proliferation and for neurodegenerative diseases associated with the Pin-1 subfamily of enzymes.

Accordingly, the invention is directed to modulators, e.g., peptide modulators, of Pin1 and Pin1-related proteins and the use of such modulators for treatment of Pin1 associated states, e.g., for the treatment of cancer.

In one embodiment, the invention provides peptides capable of inhibiting Pin1 and Pin1 related enzymes comprising the structure of formula (I):

wherein
R is 0-5 amino acid residues,
S is 0-5 amino acid residues;
Daa is any D-amino acid or D-amino acid analog;
Zaa is any amino acid or amino acid analog;
Xaa, if present, is any amino acid or amino acid analog; and
Taa, if present, is any amino acid, or amino acid analog;
Yaa is a proline or proline analog.

In one embodiment Daa is a serine. In a related embodiment, the serine further comprises a negatively charged tetra or penta valent moiety, e.g., $-OPO_3^{2-}$, $PO_3^{2-}$, $-OSO_3^{2-}$, or $-OBO_3^{2-}$.

In anther embodiment, Daa is a threonine. In a related embodiment, the threonine further comprises a negatively charged tetra or penta valent moiety, i.e., having a valence of four or five, respectively. Examples of tetra or pentavalent moieties are $-OPO_3^{2-}$, $-PO_3^{2-}$, $-OSO_3^{2-}$, and $-OBO_3^{2-}$.

In another embodiment, Taa is Gln, or a Gln analog.

In another embodiment, Xaa is a cyclic amino acid, or analog thereof. In a related embodiment, the cyclic amino acid is an aromatic amino acid. In one specific embodiment, the cyclic amino acid contains a sulfur atom, e.g., a benzothiophene moiety.

In another aspect, the invention provides a peptide capable of inhibiting the peptidyl prolyl isomerase activity of Pin1, or a Pin1-related enzyme, comprising the structure of formula (II):

Wherein
pSer is a phosphoserine residue;
R is 0-5 amino acid residues,
S is 0-5 amino acid residues;

Zaa is any amino acid or amino acid analog;
Xaa, if present, is any amino acid or amino acid analog; and
Taa, if present, is any amino acid, or amino acid analog;
Yaa is a proline or proline analog.

In one embodiment, Taa is Gln, or a Gln analog.

In another embodiment, Xaa is a cyclic amino acid, or analog thereof. In a related embodiment, the cyclic amino acid is aromatic. In a related embodiment, the aromatic amino acid, or amino acid analog, comprises a sulfur, e.g., comprises a benzothiophene (Bth).

In another embodiment, Xaa is an amino acid analog from the amino acid analogs presented in Table I. In another embodiment, Zaa is an amino acid analog selected from the amino acid analogs presented in Table I. In another related embodiment, Yaa is an amino acid analog selected from the amino acid analogs presented in Table I. In a further embodiment, Xaa, Yaa, and Zaa are residues identified in Table II.

In another embodiment, Zaa is an aromatic amino acid or analog thereof.

In another aspect, the invention provides a peptide capable of inhibiting the peptidyl prolyl isomerase activity of Pin1, or a Pin1-related enzyme, comprising the structure of formula (III):

R-Xaa-D-pThr-Yaa-Zaa-Taa-S    (III)

wherein
pThr is a phosphothreonine residue;
R is 0-5 amino acid residues,
S is 0-5 amino acid residues;
Zaa is any amino acid or amino acid analog;
Xaa, if present, is any amino acid or amino acid analog; and
Taa, if present, is any amino acid, or amino acid analog;
Yaa is a proline or proline analog.

In one embodiment, Taa is Gln, or a Gln analog.

In another embodiment, Xaa is a cyclic amino acid, or analog thereof. In a related embodiment, the cyclic amino acid is aromatic. In another embodiment, the aromatic amino acid, or amino acid analog, comprises a sulfur, e.g., comprises a benzothiophene.

In another embodiment, Zaa is an aromatic amino acid or analog thereof.

In another embodiment, Xaa is an amino acid analog from the amino acid analogs presented in Table I. In another embodiment, Zaa is an amino acid analog selected from the amino acid analogs presented in Table I. In another related embodiment, Yaa is an amino acid analog selected from the amino acid analogs presented in Table I. In a further embodiment, Xaa, Yaa, and Zaa are residues identified in Table II.

In one specific embodiment, the invention provides a peptide comprising the structure Ac-Lys($N^\epsilon$-biotinoyl)-Ala-Ala-Bth-D-Thr($PO_3H_2$)-Pip-Nal-Gln-$NH_2$. In another specific embodiment, the invention provides a peptide comprising the structure Ac-Phe-D-Thr($PO_3H_2$)-Pip-Nal-Gln-$NH_2$. The structure of the amino acid analogs depicted in the peptides represented above can be found in Table I.

In one aspect, the invention provides a library of peptides comprising peptides of having the structure of formula (I). In a related embodiment, the library is attached to a solid matrix.

In one aspect, the invention provides a method of treating a subject having a cell proliferative disorder comprising administering the subject a peptide of any one of formula (I), formula (II) or formula (III), thereby treating said subject. In one embodiment, the cell proliferative disorder is cancer.

In another aspect, the invention provides a method of treating a subject having a neurodegenerative disease comprising administering said subject the peptide of any one of formula (I), formula (II) or formula (III), thereby treating the subject. In a related embodiment, the neurodegenerative disease is Alzheimer's disease.

In another aspect, the invention provides a kit for treating a subject having a cell proliferative disorder comprising the peptide of formula (I), formula (II) or formula (III), and instructions for use. In related embodiments, the cell proliferative disorder is cancer.

In another aspect, the invention provides a kit for treating a subject having a neurodegenerative disorder comprising the peptide of formula (I), formula (II) or formula (III), and instructions for use. In a related embodiment, the neurodegenerative disorder is Alzheimer's disease.

In another aspect, the invention provides a method of screening a library of peptides for the ability to bind Pin1 comprising; contacting a matrix-bound peptide library with Pin1 or a domain thereof, for a time and under conditions sufficient for binding of said Pin1 to one or more of said peptides, and identifying said peptide or peptides that are capable of binding to Pin1 by contacting said library with a Pin1 specific antibody; thereby identifying peptides that are capable of binding to Pin1. In one embodiment, the matrix is cellulose-based.

In one embodiment, the invention provides a method of screening a library of peptides for the ability to bind phosphorylated Pin1 comprising; contacting a matrix-bound peptide library with Pin1 or a domain thereof, for a time and under conditions sufficient for binding of said Pin1 to one or more of said peptides, and identifying said peptide or peptides that are capable of binding to Pin1 by contacting said library with a Pin1 specific antibody; thereby identifying peptides that are capable of binding to Pin1. Pin1 can be phosphorylated, for example, on serine 16. In one embodiment, the matrix is cellulose-based.

In a related embodiment, the fragment of Pin1 comprises the peptidyl-prolyl isomerase domain, e.g., amino acid residues from about residue 51 to about residue 153 of human Pin1.

In another aspect, the invention provides a method of designing a high affinity inhibitor of Pin1 comprising; designing a peptide that specifically interacts with the Pin1 active site; wherein said peptide forms an intramolecular hydrogen bond between a carbonyl oxygen and a backbone amide; wherein said carbonyl oxygen and backbone amide are on amino acid residues that are four residues apart; thereby designing a high affinity inhibitor of Pin1.

In a related embodiment, the peptide is five residues in length. In one embodiment, the carbonyl oxygen is from a phenylalanine, or analog thereof. In one embodiment, the backbone amide is from an aromatic amino acid residue, or analog thereof.

In one embodiment the hydrogen bond is between a carbonyl oxygen from a phenylalanine, or analog thereof, and an aromatic amino acid, or analog thereof.

In one aspect, the invention provides a peptide inhibitor of Pin1 that forms an intramolecular hydrogen bond when bound to Pin1. In one embodiment, the intramolecular hydrogen bond is between a carbonyl oxygen and a backbone amide.

In a related embodiment, the peptide inhibitor has the structure,

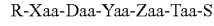

R-Xaa-Daa-Yaa-Zaa-Taa-S wherein
R is 0-5 amino acid residues;
S is 0-5 amino acid residues;
Daa is any D-amino acid or D-amino acid analog;

Zaa is any amino acid or amino acid analog;
Xaa, if present, is any amino acid or amino acid analog;
Taa, if present, is any amino acid, or amino acid analog; and
Yaa is a proline or proline analog.

BRIEF DESCRIPTION OF THE DRAWINGS

FIG. 2A depicts the binding preferences of the PPIase and WW domain of hPin1 regarding peptide 15. In far western blot related experiments, increasing amounts (from left to right: 1, 5, 10, 52.5, 105 pmol) of GST, GST-hPin1 or its single GST-hPin1 PPIase and GST-hPin1 WW domain were spotted onto nitrocellulose membranes followed by a blocking procedure. The membranes were then incubated with a 1 µM solution of peptide 15 or 50 µM solution of its nonphosphorylated derivative (control). Signals were detected after incubation of the nitrocellulose membranes with horseradish peroxidase-conjugated streptavidin followed by a chemiluminescent reaction using the SuperSignal® substrate. FIG. 2B depicts an analysis of the binding of peptide 15 towards different GST-hPin1 variants. The indicated amounts of peptide 15 were spotted onto nitrocellulose membranes followed by a blocking procedure and incubation with the respective GST-hPin1 variant. To detect specifically the bound protein, the membranes were incubated with an anti hPin1 PPIase domain antiserum as primary antibody and horseradish peroxidase-conjugated secondary antibody. Visualization was done using the SuperSignal® substrate. Residual PPIase activities of GST-hPin1 and its variants were determined according to Zhou et al., 2000 and/or Yaffe et al., 1997. The PPIase activity of the GST-hPin1 variant Ser16Glu was measured in the protease free PPIase assay.

FIG. 3A depicts peaks that represent the heat evolved after injection of peptide 17 into the sample cell containing hPin1. After the 11$^{th}$ injection only the heat of dilution is observed. The experiment was performed at 10 C. FIG. 3B depicts integrals of the corresponding peaks of panel A are plotted against the molar ratio of peptide 17 and hPin1. The solid line represents a nonlinear least squares fit analysis of the binding heat assuming a single binding site model with the following parameters: $\Delta H_{bind}$=−4561±36 cal/mol, $T\Delta S_{bind}$=5433±529 cal/mol, n=0.96 (binding stoichiometry) and $K_{Ass}$=5.18×10$^7$±7×10$^6$ M$^{-1}$ (association constant). The dissociation constant $K_D$ was calculated from the equation $K_D$=1/$K_{Ass}$ with $K_D$=19.3±2.6 nM.

FIG. 5A depicts the indicated concentrations of peptide 16 were incubated with *X. laevis* embryo extract in the absence of phosphatase inhibitors. Peptide 16/XlPin1-complex was then extracted from the respective mixture using streptavidin sepharose. Samples were analyzed regarding coextracted XlPin1 by SDS PAGE followed by western blot analysis. Untreated lysate (input) was loaded as a control. Authentic XlPin1 was detected using an anti hPin1 PPIase domain antiserum followed by incubation with a horseradish peroxidase-conjugated secondary antibody. Visualization was done using the SuperSignal® substrate. FIG. 5B indicates concentrations of peptide 16 were incubated with HeLa cell lysate in the absence of phosphatase inhibitors. The peptide 16/hPin1-complex was then precipitated from the respective mixture using streptavidin sepharose and isolated from the supernatant. Extracted proteins and the supernatants were then analyzed by SDS PAGE. In both cases, untreated HeLa cell lysate was loaded as a control. After western blotting, hPin1 was detected using an anti hPin1 PPIase domain antiserum as primary antibody and a horseradish peroxidase-conjugated secondary antibody. Visualization was done by a chemiluminescent reaction using the SuperSignal® substrate.

FIG. 10A depicts the time course of V5-tagged hPin1 expression was analyzed by preparation of *X. laevis* embryo lysate 1, 2 and 4 hours after injection of 1, 2 or 3 ng of V5-tagged hPin1 mRNA. In every case, the injected volume was 10 nl. Lysates were prepared in lysis buffer containing phosphatase and protease inhibitors. Samples were separated by SDS PAGE followed by western blotting. Endogenous XlPin1 and V5-tagged hPin1 were detected using an anti hPin1 PPIase domain antiserum as primary antibody followed by incubation with a horseradish peroxidase-conjugated secondary antibody. Visualization was done using the SuperSignal® substrate. FIG. 10B indicates that rescue by peptide 17 caused block in cell division, 250 pmol of peptide 17 were coinjected with 0-3 ng mRNA of V5-tagged hPin1 in *X. laevis* embryos. In every case, the whole volume of injection was 10 nl. The indicated amount of the mRNA was injected in the animal half of 30 embryos at stage 2 of development. Embryos with large and/or apoptotic appearing cells surrounded by normally developed cells were counted after additional 5 hours of development (stage 8-9). The percentage of vital embryos that did not show any special phenotypic features after injection was determined. Each percentage of vital embryos shown in the figure is the average of four independent experiments. FIG. 10C indicates the expression of V5-tagged hPin1 variants was evaluated by preparation of embryo lysate after 4 hours of injection of the respective mRNA (2 ng) in *X. laevis* embryos. Lysates were prepared in lysis buffer containing phosphatase and protease inhibitors. Samples were separated using SDS PAGE followed by western blot analysis. Endogenous XlPin1 and injected V5-tagged hPin1 variants were detected using an anti hPin1 PPIase domain antiserum as primary antibody and a horseradish peroxidase-conjugated secondary antibody. Visualization was done by a chemiluminescent reaction using the SuperSignal® substrate (Pierce). FIG. 10D depicts 250 pmol of peptide 17 was coinjected with 2 ng mRNA of the indicated V5-tagged hPin1 variant (whole volume 10 nl) in the animal half of 30 *X. laevis* embryos at stage 2 of development. Results were analyzed as described for FIG. 10B. Each percentage of vital embryos shown in the figure is the average of four independent experiments.

DETAILED DESCRIPTION OF THE INVENTION

Figure 1:
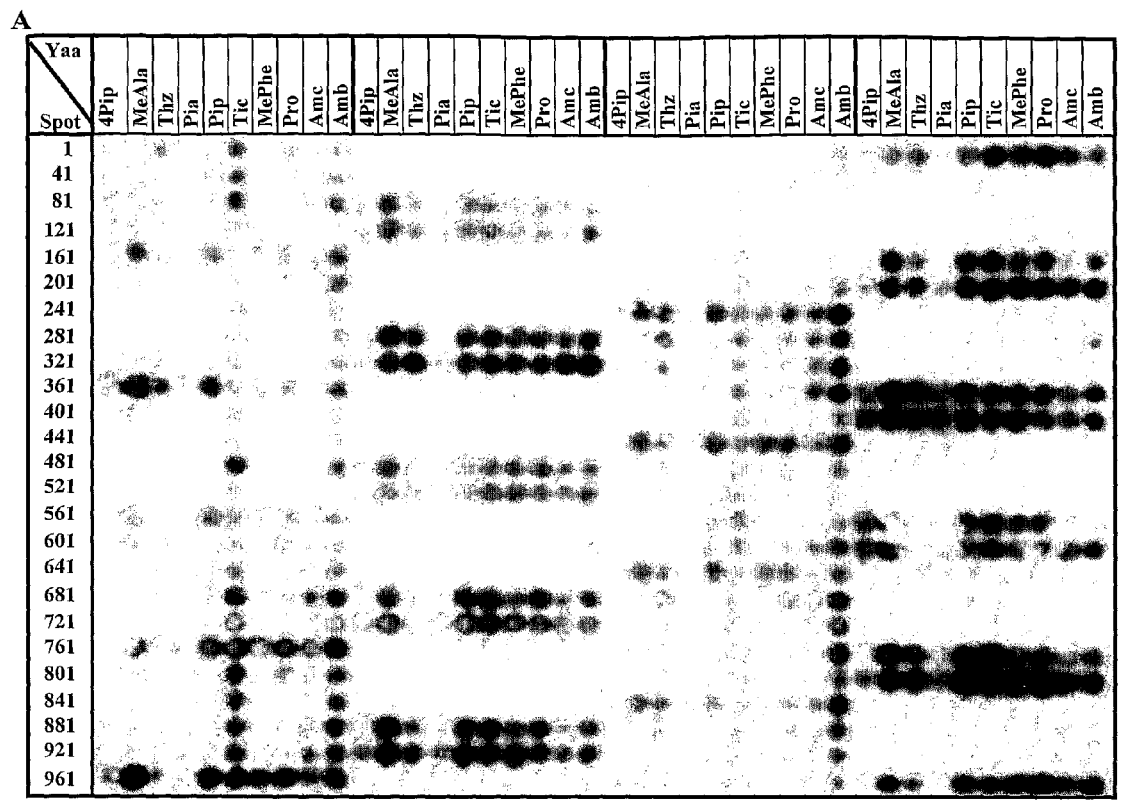
FIGS. 1A-B depicts a screening experiment of a cellulose-bound combinatorial peptide library for substrate-like Pin1 ligands. The library was created by standard automated Spot synthesis on a cellulose membrane. The library was composed of 1000 peptides with the general structure Ac-Xaa-Thr($PO_3H_2$)-Yaa-Zaa-NHCH(($CH_2$)$_2$CONH-linker)COOH. The peptides were cellulose-anchored via a secondary amide bond formed by condensation of the amino group of the β-alanyl-β-alanine linker attached to the cellulose and the carboxyl group of the glutamic acid side chain of the peptides. Screening was performed by incubating of the library with the recombinant hPin1 PPIase domain followed by electroblotting of the bound protein to a nitrocellulose membrane. The hPin1 PPIase domain bound to the spots was then detected using an anti hPin1 PPIase domain antiserum (rabbit) as primary antibody and an anti rabbit specific, horseradish peroxidase-conjugated secondary antibody. Visualization was done by a chemiluminescent reaction using the SuperSignal® substrate (Pierce). The numbers indicated on the left side of the figure represent the number of the first spot of each horizontal line. The residue Yaa can be read from the label on the top of the according row. The structures of Yaa are shown in Table I. The table shows the sequence key for the positions Xaa and Zaa. Xaa changes after every hundred spots and can be read from the horizontal line of the appropriate range. Zaa changes after every ten spots and can be read from the vertical line according to the number of the spot. The structures of Xaa and Zaa are shown in Table I.

The invention is directed to modulators, e.g., peptide modulators, of Pin1 and Pin1-related proteins and the use of such modulators for treatment of Pin1 associated disorders, e.g., diseases and disorders characterized by a misexpression or misregulation of Pin1.

Compositions

The present invention pertains, at least in part, to compositions that modulate the activity of Pin1, or a Pin1 related enzyme. For example, the invention provides Pin1-modulating compounds having formula (I), formula (II), or formula (III) as described herein.

In one embodiment, the invention provides peptides capable of inhibiting Pin1 and Pin1 related enzymes comprising the structure of formula (I):

R-Xaa-Daa-Yaa-Zaa-Taa-S    (I)

Wherein
R is 0-5 amino acid residues,
S is 0-5 amino acid residues;
Daa is any D-amino acid or D-amino acid analog;
Zaa is any amino acid or amino acid analog;
Xaa, if present, is any amino acid or amino acid analog; and
Taa, if present, is any amino acid, or amino acid analog;
Yaa is a proline or proline analog.

In one embodiment Daa is a serine. In a related embodiment, the serine further comprises a negatively charged tetra or penta valent moiety, e.g., —$OPO_3^{2-}$, —$PO_3^{2-}$, —$OSO_3^{2-}$, or —$OBO_3^{2-}$.

In another embodiment, Daa is a threonine. In a related embodiment, the threonine further comprises a negatively charged tetra or penta valent moiety, e.g., —$OPO_3^{2-}$, —$PO_3^{2-}$, —$OSO_3^{2-}$, or —$OBO_3^{2-}$.

In another embodiment, Taa is Gln, or a Gln analog.

In another embodiment, Xaa is a cyclic amino acid, or analog thereof. In a related embodiment, the cyclic amino acid is an aromatic amino acid. In one specific embodiment, the cyclic amino acid contains a sulfur atom, e.g., a benzothiophene moiety.

In another aspect, the invention provides a peptide capable of inhibiting the peptidyl prolyl isomerase activity of Pin1, or a Pin1-related enzyme, comprising the structure of formula (II):

R-Xaa-D-pSer-Yaa-Zaa-Taa-S    (II)

wherein
pSer is a phosphoserine residue;
R is 0-5 amino acid residues,

S is 0-5 amino acid residues;
Zaa is any amino acid or amino acid analog;
Xaa, if present, is any amino acid or amino acid analog; and
Taa, if present, is any amino acid, or amino acid analog;
Yaa is a proline or proline analog.

In one embodiment, Taa is Gln, or a Gln analog.

In another embodiment, Xaa is a cyclic amino acid, or analog thereof. In a related embodiment, the cyclic amino acid is aromatic. In a related embodiment, the aromatic amino acid, or amino acid analog, comprises a sulfur, e.g., comprises a benzothiophene.

In another embodiment, Xaa is an amino acid analog from the amino acid analogs presented in Table I. In another embodiment, Zaa is an amino acid analog selected from the amino acid analogs presented in Table I. In another related embodiment, Yaa is an amino acid analog selected from the amino acid analogs presented in Table I. In a further embodiment, Xaa, Yaa, and Zaa are residues identified in Table II.

TABLE I

| H-Xaa-OH and H-Zaa-OH | | H-Yaa-OH | |
|---|---|---|---|
|  | 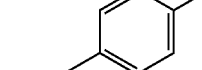 |  |  |
| 2-Aminobenzoic acid<br>H-Abz-OH | β-(4-Biphenylyl)-alanine<br>H-Bip-OH | 4-Aminomethyl-benzoic acid<br>H-Amb-OH | 4-Aminomethyl-cyclohexane-<br>carboxylic acid<br>H-Amc-OH |
|  |  |  |  |
| β-(3-Benzothienyl)-alanine<br>H-Bth-OH | β-Cyclohexyl-alanine<br>H-Cha-OH | $N^\alpha$-Methyl-alanine<br>H-MeAla-OH | $N^\alpha$-Methyl-phenylalanine<br>H-MePhe-OH |
|  |  |  |  |
| α,α-Dibutyl-glycine<br>H-Dbg-OH | β-(2-Naphtyl)-alanine<br>H-Nal-OH | 4-Piperidinyl-acetic acid<br>H-Pia-OH | Piperidine-2-carboxylic acid<br>H-Pip-OH |
|  |  |  |  |
| α-tButyl-glycine<br>H-tBuGly-OH | 4-tButyl-phenylalanine<br>H-tBuPhe-OH | Piperidine-4-carboxylic acid<br>H-4Pip-OH | Thiazolidine-4-carboxylic acid<br>H-Thz-OH |

TABLE I-continued

| H-Xaa-OH and H-Zaa-OH | H-Yaa-OH |
|---|---|
| β-(2-Thienyl)-alanine H-Thi-OH | 1,2,3,4-Tetrahydro-isoquinoline-3-carboxylic acid H-Tic-OH |

TABLE II

| Peptide | Residues in position | | | $IC_{50}(\mu M)$ |
|---|---|---|---|---|
| | Xaa | Yaa | Zaa | |
| 1 | tBuPhe | Pro | Nal | 30 |
| 2 | Thi | Pro | Bip | 22 |
| 3 | Bth | Pro | Cha | >50 |
| 4 | Bth | Pro | Nal | 20 |
| 5 | Bip | Pro | Bth | 15 |
| 6 | Bip | Pro | Nal | 18 |
| 7 | Nal | Pro | tBuGly | >50 |
| 8 | Nal | Pro | Cha | >50 |
| 9 | tBuPhe | MeAla | Nal | 10 |
| 10 | Thi | MeAla | Nal | 15 |
| 11 | Cha | MeAla | Nal | 7 |
| 12 | Phe | MeAla | Bth | 20 |
| 13 | tBuPhe | Tic | Bth | 8 |
| 14 | Cha | Tic | Nal | 25 |
| 15 | Bth | Pip | Nal | 0.21 |

In another embodiment, Zaa is an aromatic amino acid or analog thereof.

In another aspect, the invention provides a peptide capable of inhibiting the peptidyl prolyl isomerase activity of Pin1, or a Pin1-related enzyme, comprising the structure of formula (III):

R-Xaa-D-pThr-Yaa-Zaa-Taa-S          (III)

wherein
pThr is a phosphothreonine residue;
R is 0-5 amino acid residues,
S is 0-5 amino acid residues;
Zaa is any amino acid or amino acid analog;
Xaa, if present, is any amino acid or amino acid analog; and
Taa, if present, is any amino acid, or amino acid analog;
Yaa is a proline or proline analog.

In one embodiment, Taa is Gln, or a Gln analog.

In another embodiment, Xaa is a cyclic amino acid, or analog thereof. In a related embodiment, the cyclic amino acid is aromatic. In another embodiment, the aromatic amino acid, or amino acid analog, comprises a sulfur, e.g., comprises a benzothiophene.

In another embodiment, Zaa is an aromatic amino acid or analog thereof.

In another embodiment, Xaa is an amino acid analog from the amino acid analogs presented in Table I. In another embodiment, Zaa is an amino acid analog selected from the amino acid analogs presented in Table I. In another related embodiment, Yaa is an amino acid analog selected from the amino acid analogs presented in Table I. In a further embodiment, Xaa, Yaa, and Zaa are residues identified in Table II.

In one specific embodiment, the invention provides a peptide comprising the structure Ac-Lys($N^\epsilon$-biotinoyl)-Ala-Ala-Bth-D-Thr($PO_3H_2$)-Pip-Nal-Gln-$NH_2$. In another specific embodiment, the invention provides a peptide comprising the structure Ac-Phe-D-Thr($PO_3H_2$)-Pip-Nal-Gln-$NH_2$. As demonstrated in the examples, the use of a D-isomer at position Daa increases binding affinity of the peptide inhibitor. Accordingly, the inhibitors of the invention have a D-amino acid at position Daa to increase the binding affinity of the peptides to Pin1.

In one aspect, the invention provides a library of peptides comprising peptides of having the structure of formula (I). In a related embodiment, the library is attached to a solid matrix.

In one embodiment, the peptides of formula (I), formula (II), or formula (III). are linear peptides having free N and C terminal residues. In another embodiment, the peptides are cyclic peptides having the N and C terminal residues covalently attached.

In some embodiments, Xaa and Zaa are cyclic or aromatic amino acid residues, or amino acid analogs.

In particular embodiments, Xaa, Zaa, and Yaa are any amino acid analog indicated in Table I.

The term "D-amino acid" is intended to include an amino acid residue, or analog thereof, with D stereochemistry around its stereocenter.

The term "proline analog" is intended to include any amino acid mimetic that is either cyclic or non-cyclic. The proline analog may or may not contain a nitrogen in the amino acid side chain. If the proline analog is a cyclic structure, it may have a 4-7 member substituted or unsubstituted heterocyclic group, e.g., imidazolyl, pyrrolyl, tropolonyl, phenyl, or camphoryl.

The compounds of the invention may be phosphorylated or unphosphorylated and therefore preferentially bind to unphosphorylated or phosphorylated Pin1.

Peptides of the invention can be made synthetically as known by one of skill in the art. Peptide synthesis is described, for example, in Combinatorial Peptide Library Protocols (1987) Volume #: 87, edited by Shmuel Cabilly. Further, companies such as Jerini (Berlin, Germany) and Sigma-Genosys (The Woodlands, Tex.) specialize in for-hire peptides synthesis. Exemplary synthetic methods are set forth in the Examples section.

Co-Crystals of Pin1 and Peptides of the Invention

The instant invention provides a crystal structure of Pin1 complexed with a peptide of the invention. This peptide co-crystal allows for one of skill in the art to determine residues that are important in developing modulators of Pin1. Conditions and methods used to grow crystals of Pin1 co-complexes are described in the examples and further in WO 03/074001A2, the entire contents of which is expressly incorporated herein by reference.

The methods described in WO 03/074001A2 allow for the definition of five areas of the active site to which peptides of the invention may bind. The five areas are defined below.

The first area is the "hydrophobic pocket." The hydrophobic pocket refers to the portion of the active site that binds a hydrophobic moiety. In one embodiment, the hydrophobic pocket contains 4, 6, 8, 10, 12 or 14 hydrophobic amino acid residues. In one particular embodiment, the hydrophobic pocket contains amino acid residues His59, Leu61, Leu122, Met130, Gln131, Phe134, Thr152, and His157 of Pin1.

The second area is the "cysteine/serine valley." The cysteine/serine valley refers to a portion of the active site that is responsible for binding or interacting with the isomerized peptide bond moiety of the substrate. In one embodiment this region contains residues Leu61, Cys113 and Ser154 of Pin1.

The third area is the "phosphate binding pocket." The phosphate binding pocket refers to a region of the active site containing three positively charged amino acids that binds or interacts with negatively charged moieties or hydrogen donor/acceptor groups. In one embodiment, this pocket is contains 4, 6, 8, or 10 amino acid residues. In one particular embodiment, this pocket is defined by residues Lys63, Ser67, Arg68, Arg69, Pro70 and Ser154.

The fourth area is the "substrate entry groove." The substrate entry groove refers to a region of the polypeptide that allows for substrate entry into the active site. In one embodiment this groove contains amino acids Lys63, Arg69, Ser71, Ser72, Trp73, Arg74, Gln75, Glu76, Asp112, Cys113, and Ser114.

The fifth area is the "lip region." The lip region refers to the residues that surround the active site cavity, as defined previously. In one embodiment these lip regions contain residues that are within 10 Å of the active site cavity. In one particular embodiment, this lip region is defined by, but not limited to, residues Arg54, Arg56, His64, Ser65, Gln66, Lys77, Ile78, Thr79, Ser115, Lys117, Ala118, Gly123, Ala124, Phe125, Ser126, Arg127, Gly128, Gln129, Pro133, Glu135, Lys132, Phe151, Asp153, Gly155, and Ile156.

In one embodiment, the peptide inhibitors of the invention interact with 5, 6, 7, 8, 9, 10, 11, 12, 13, 14, 15 or more of these residues. In one embodiment, the peptide inhibitors of the invention interact with Leu61, Lys63, Arg68, Phe125, Phe134, Met130, Gln129, Ser154, and Gln131.

Methods

The present invention pertains, at least in part, to a method for treating a Pin1-associated disorder in a subject. For example, the method includes administering to the subject an effective amount of a Pin1-modulating compound of the invention having formula (I), formula (II), or formula (III).

In an additional embodiment, the invention pertains, at least in part, to a method for treating a Pin1 associated disorder in a subject. This method includes administering to the subject an effective amount of a Pin1-modulating compound of formula (I), formula (II), and formula (III), as described above, such that the Pin1 associated disorder is treated. In certain embodiments, the overexpression of Pin1 is associated with the presence of cancer in the subject.

Additionally, Pin1 may cause changes in the expression, e.g., underexpression or overexpression of endogenous cyclin D1. In fact, Pin1 is believed to regulate, e.g., activate, the expression of cyclin D1 by acting cooperatively with c-Jun to activate the cyclin D1 promoter. In order to activate cyclin D1 expression, c-Jun must be phosphorylated. Pin1 binds to c-Jun mainly via phosphorylated $S^{63/73}$-P motifs. Pin1 activates phosphorylated c-Jun to induce cyclin D1 expression by regulating the conformation of the phosphorylated S—P motifs in c-Jun.

The term "Pin1-associated state" or "Pin1 associated disorder" includes disorders and states (e.g., a disease state) that are associated with the misexpression or misregulation of Pin1. This misexpression or misregulation can be as a result of the altered production, degradation, or regulation of Pin1, e.g., the phosphorylation/dephosphorylation of Pin1. Without being bound by theory, Pin1 associated disorders that are related to higher than necessary levels of Pin1 can be caused by (1) an increase in the level of transcription or translation, or a decrease in the level of degradation, of Pin1 such that an abnormally high amount of Pin1 polypeptide is present in a cell, or (2) the amount Pin1 that is present in the unphosphorylated, i.e., active form, is abnormally high due to either an increase in the dephosphorylation of Pin1 or a decrease in the phosphorylation of Pin1. Pin1 disorders are often associated with abnormal cell growth, abnormal cell proliferation, or misexpression of Pin1 (e.g., Pin1 protein or nucleic acid). Pin1-associated states include states resulting from an elevation in the expression of cyclin D1 and/or Pin1. Pin1-associated states also include states resulting from an elevation in the phosphorylation level of c-Jun, particularly phosphorylation of c-Jun on $Ser^{63/73}$-Pro and/or from an elevation in the level of c-Jun amino terminal kinases (JNKs) present in a cell. Pin1-associated states include neoplasia, cancer, undesirable cell growth, and/or tumor growth. Pin1-associated states include states caused by DNA damage, an oncogenic protein (i.e. Ha-Ras), loss of or reduced expression of a tumor suppressor (i.e. Brca1), and/or growth factors. Pin1-associated state is also intended to include diseases or disorders caused by, or associated with, deregulation of genes and/or gene products involved in a biological pathway that includes Pin1 and/or cyclin D1 (e.g. beta-catenin, APC or WNT). Beta-catenin, APC and WNT have been linked to cancer development as demonstrated in Biochim Biophys Acta. (2003) 1653: 1-24 and Eur J Surg Oncol. (2003) 29: 107-117. Pin1 associated states further include disorders and states associated with regulation or activity of Pin1 in the brain, e.g., neurodegenerative disorders such as Alzheimer's disease, wherein the phosphorylation state of tau is influenced by the activity of Pin1 (see, for example, Lu, K P (2004) Trends Biochem Sci. 29(4):200-9).

Pin associated states can also include states characterized by infection. The compounds of the invention are useful in inhibiting mitosis in pathogenic organisms and are, therefore, useful for treating infectious diseases. Particular infectious diseases treatable by the methods disclosed herein include bacterial infections and fungal infections.

Bacterial infections contemplated for treatment using invention compounds and methods include infections caused by both gram-positive and gram-negative bacteria, including infections caused by *Staphylococcus, Clostridium, Streptococcus, Enterococcus, Diplococcus, Hemophilus, Neisseria, Erysipelothricosis, Listeria, Bacillus, Salmonella, Shigella, Escherichia, Klebsiella, Enterobacter, Serratia, Proteus, Morganella, Providencia, Yersinia, Camphylobacter, Mycobacteria,* and the like. Infection by such organisms causes a wide variety of disorders including pneumonia, diarrhea and dysentery, anthrax, rheumatic fever, toxic shock syndrome, mastoiditis, meningitis, gonorrhea, typhoid fever, gastroenteritis, brucellosis, cholera, bubonic plague, tetanus, tuberculosis, Lyme disease, and the like.

Fungal infections contemplated for treatment using invention compounds and methods include systemic fungal infections, dermatophytoses and fungal infections of the genito-unrinary tract. Systemic fungal infections include those caused by *Histoplasma, Coccidioides, Cryptococcus, Blastocyces, Paracoccidioides,*

*Candida, Aspergillus, Nocardia, Sporothrix, Rhizopus, Absidia, Mucor, Hormodendrum, Phialophora, Rhinosporidium*, and the like. Dermatophyte infections include those caused by *Microsporum, Trichophyton, Epidermophyton, Candida, Pityiosporum*, and the like. Fungal disorders of the genito-urinary tract include infections caused by *Candida, Cryptococcus, Aspergillus, Zygomycodoides*, and the like. Infection by such organisms causes a wide variety of disorders such as ringworm, thrush, San Joaquin fever or Valley fever, Gilcrist's disease, and the like. These infections can be particularly serious, and even fatal, in patients with a depressed immune system such as organ transplant recipients and persons with acquired immunodeficiency syndrome (AIDS).

The terms "misexpression" and "misregulation" are used interchangeably herein. These terms are intended to include non-wild type pattern of gene expression or regulation. Expression and regulation as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences. Misregulation can include aberrant levels of phosphorylation of the enzyme.

The term "cell proliferative disorder" is intended to include diseases and disorders characterized by abnormal cell growth. Included in these diseases and disorders are carcinomas, sarcomas, mylomas, and neoplasias. Exemplary types of cell proliferative disorders include as used herein the term "cell proliferative disorder" includes diseases and disorders such as oligodendroglioma, astrocytoma, glioblastomamultiforme, cervical carcinoma, endometrioid carcinoma, endometrium serous carcenoma, ovary endometrioid cancer, ovary Brenner tumor, ovary mucinous cancer, ovary serous cancer, uterus carcinosarcoma, breast cancer, breast lobular cancer, breast ductal cancer, breast medullary cancer, breast mucinous cancer, breast tubular cancer, thyroid adenocarcinoma, thyroid follicular cancer, thyroid medullary cancer, thyroid papillary carcinoma, parathyroid adenocarcinoma, adrenal gland adenoma, adrenal gland cancer, pheochromocytoma, colon adenoma mild displasia, colon adenoma moderate displasia, colon adenoma severe displasia, colon adenocarcinoma, esophagus adenocarcinoma, hepatocellular carcinoma, mouth cancer, gall bladder adenocarcinoma, pancreatic adenocarcinoma, small intestine adenocarcinoma, stomach diffuse adenocarcinoma, prostate (hormone-refract), prostate (untreated), kidney chromophobic carcinoma, kidney clear cell carcinoma, kidney oncocytoma, kidney papillary carcinoma, testis non-seminomatous cancer, testis seminoma, urinary bladder transitional carcinoma, lung adenocarcinoma, lung large cell cancer, lung small cell cancer, lung squamous cell carcinoma, Hodgkin lymphoma, MALT lymphoma, non-hodgkins lymphoma (NHL) diffuse large B, NHL, thymoma, skin malignant melanoma, skin basalioma, skin squamous cell cancer, skin merkel zell cancer, skin benign nevus, lipoma, and liposarcoma.

The term "phosphorylation state" is intended to denote that the Pin1 polypeptide can exist in either a phosphorylated or unphosphorylated state. The phosphorylation state denotes whether the Pin1 in a biological sample is phosphorylated or unphosphorylated, or the relative ratios of phosphorylated to unphosphorylated Pin1 in a sample. For example, Lu et al. ((2002) J Biol Chem. 277: 2381-4) demonstrated the importance of the phosphorylation of serine 16 on the ability of Pin1 to bind phosphorylated substrate.

The term "neurodegenerative" as used herein, is used to designate a group of disorders in which there is gradual, progressive wasting away of structural elements of the nervous system. As used herein, the term "neurodegenerative phenotype" includes any parameter related to neurodegeneration, e.g., a reduction in mobility, a reduction in vocalization, abnormal limb-clasping reflex, retinal atrophy inability to succeed in a hang test, an increased level of MPM-2, an increased level of neurofibril tangles, increased tau phosphorylation, tau filament formation, abnormal neuronal morphology, lysosomal abnormalities, neuronal degeneration, and gliosis.

As used herein, the term "neurodegenerative disease or disorder" includes any disease disorder or condition that affects neuronal homeostasis, e.g., results in the degeneration or loss of neuronal cells. Neurodegenerative diseases include conditions in which the development of the neurons, i.e., motor or brain neurons, is abnormal, as well as conditions in which result in loss of normal neuron function. Examples of such neurodegenerative disorders include Alzheimer's disease, Pick disease, progressive supranuclear palsy, corticobasal degeneration, frontaltemporal dementia and parkinsonism linked to chromosome 17.

"Neoplasia" or "neoplastic transformation" is the pathologic process that results in the formation and growth of a neoplasm, tissue mass, or tumor. Such processes include uncontrolled cell growth, including either benign or malignant tumors. Neoplasms include abnormal masses of tissue, the growth of which exceeds and is uncoordinated with that of the normal tissues and persists in the same excessive manner after cessation of the stimuli that evoked the change. Neoplasms may show a partial or complete lack of structural organization and functional coordination with the normal tissue, and usually form a distinct mass of tissue. One cause of neoplasia is dysregulation of the cell cycle machinery.

Neoplasms tend to grow and function somewhat independently of the homeostatic mechanisms that control normal tissue growth and function. However, some neoplasms remain under the control of the homeostatic mechanisms that control normal tissue growth and function. For example, some neoplasms are estrogen sensitive and can be arrested by anti-estrogen therapy. Neoplasms can range in size from less than 1 cm to over 6 inches in diameter. A neoplasm even 1 cm in diameter can cause biliary obstructions and jaundice, if it arises in and obstructs the ampulla of Vater.

Neoplasms tend to morphologically and functionally resemble the tissue from which they originated. For example, neoplasms arising within the islet tissue of the pancreas resemble the islet tissue, contain secretory granules, and secrete insulin. Clinical features of a neoplasm may result from the function of the tissue from which it originated. For example, excessive amounts of insulin can be produced by islet cell neoplasms resulting in hypoglycemia which, in turn, results in headaches and dizziness. However, some neoplasms show little morphological or functional resemblance to the tissue from which they originated. Some neoplasms result in such non-specific systemic effects as cachexia, increased susceptibility to infection, and fever.

By assessing the histology and other features of a neoplasm, it can be determined whether the neoplasm is benign or malignant. Invasion and metastasis (the spread of the neoplasm to distant sites) are definitive attributes of malignancy. Despite the fact that benign neoplasms may attain enormous size, they remain discrete and distinct from the adjacent non-neoplastic tissue. Benign tumors are generally well circumscribed and round, have a capsule, and have a grey or white color, and a uniform texture. In contrast, malignant tumors generally have fingerlike projections, irregular margins, are not circumscribed, and have a variable color and texture. Benign tumors grow by pushing on adjacent tissue as they grow. As the benign tumor enlarges it compresses adjacent tissue, sometimes causing atrophy. The junction between a benign tumor and surrounding tissue may be converted to a fibrous connective tissue capsule allowing for easy surgical removal of the benign tumor.

Conversely, malignant tumors are locally invasive and grow into the adjacent tissues usually giving rise to irregular margins that are not encapsulated making it necessary to remove a wide margin of normal tissue for the surgical removal of malignant tumors. Benign neoplasms tend to grow more slowly and tend to be less autonomous than malignant tumors. Benign neoplasms tend to closely histologically resemble the tissue from which they originated. More highly differentiated cancers, i.e., cancers that resemble the tissue from which they originated, tend to have a better prognosis than poorly differentiated cancers, while malignant tumors are more likely than benign tumors to have an aberrant function, e.g., the secretion of abnormal or excessive quantities of hormones.

The histological features of cancer are summarized by the term "anaplasia." Malignant neoplasms often contain numerous mitotic cells. These cells are typically abnormal. Such mitotic aberrations account for some of the karyotypic abnormalities found in most cancers. Bizarre multinucleated cells are also seen in some cancers, especially those that are highly anaplastic.

The term "anaplasia" includes histological features of cancer. These features include derangement of the normal tissue architecture, the crowding of cells, lack of cellular orientation termed dyspolarity, and cellular heterogeneity in size and shape termed "pleomorphism." The cytologic features of anaplasia include an increased nuclear-cytoplasmic ratio (nuclear-cytoplasmic ratio can be over 50% for malignant cells), nuclear pleomorphism, clumping of the nuclear chromatin along the nuclear membrane, increased staining of the nuclear chromatin, simplified endoplasmic reticulum, increased free ribosomes, pleomorphism of mitochondria, decreased size and number of organelles, enlarged and increased numbers of nucleoli, and sometimes the presence of intermediate filaments.

The term "dysplasia" includes pre-malignant states in which a tissue demonstrates histologic and cytologic features intermediate between normal and anaplastic. Dysplasia is often reversible.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The term "carcinoma" includes malignancies of epithelial or endocrine tissues, including respiratory system carcinomas, gastrointestinal system carcinomas, genitourinary system carcinomas, testicular carcinomas, breast carcinomas, prostate carcinomas, endocrine system carcinomas, melanomas, choriocarcinoma, and carcinomas of the cervix, lung, head and neck, colon, and ovary. The term "carcinoma" also includes carcinosarcomas, which include malignant tumors composed of carcinomatous and sarcomatous tissues. The term "adenocarcinoma" includes carcinomas derived from glandular tissue or a tumor in which the tumor cells form recognizable glandular structures.

The term "sarcoma" includes malignant tumors of mesodermal connective tissue, e.g., tumors of bone, fat, and cartilage.

The terms "leukemia" and "lymphoma" include malignancies of the hematopoietic cells of the bone marrow. Leukemias tend to proliferate as single cells, whereas lymphomas tend to proliferate as solid tumor masses. Examples of leukemias include acute myeloid leukemia (AML), acute promyelocytic leukemia, chronic myelogenous leukemia, mixed-lineage leukemia, acute monoblastic leukemia, acute lymphoblastic leukemia, acute non-lymphoblastic leukemia, blastic mantle cell leukemia, myelodysplastic syndrome, T cell leukemia, B cell leukemia, and chronic lymphocytic leukemia. Examples of lymphomas include Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

For example, the therapeutic methods of the present invention can be applied to cancerous cells of mesenchymal origin, such as those producing sarcomas (e.g., fibrosarcoma, myxosarcoma, liposarcoma, chondrosarcoma, osteogenic sarcoma or chondosarcoma, angiosarcoma, endotheliosarcoma, lymphangiosarcoma, synoviosarcoma or mesotheliosarcoma); leukemias and lymphomas such as granulocytic leukemia, monocytic leukemia, lymphocytic leukemia, malignant lymphoma, plasmocytoma, reticulum cell sarcoma, or Hodgkin's disease; sarcomas such as leiomyosarcoma or rhabdomyosarcoma, tumors of epithelial origin such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, chorioaencinoma, semonoma, or embryonal carcinoma; and tumors of the nervous system including gioma, menigoma, medulloblastoma, schwannoma or epidymoma. Additional cell types amenable to treatment according to the methods described herein include those giving rise to mammary carcinomas, gastrointestinal carcinoma, such as colonic carcinomas, bladder carcinoma, prostate carcinoma, and squamous cell carcinoma of the neck and head region. Examples of cancers amenable to treatment according to the methods described herein include vaginal, cervical, and breast cancers.

The language "inhibiting undesirable cell growth" is intended to include the inhibition of undesirable or inappropriate cell growth. The inhibition is intended to include inhibition of cell proliferation, including rapid proliferation. For example, undesirable cell growth can result in benign masses or malignant tumors. Examples of benign conditions which result from inappropriate cell growth or angiogenesis are diabetic retinopathy, retrolental fibroplasia, neovascular glaucoma, psoriasis, angiofibromas, rheumatoid arthritis, hemangiomas, Karposi's sarcoma, and other conditions or dysfunctions characterized by dysregulated endothelial cell division.

The language "inhibiting tumor growth" or "inhibiting neoplasia" includes the prevention of the growth of a tumor in a subject or a reduction in the growth of a pre-existing tumor in a subject. The inhibition also can be the inhibition of the metastasis of a tumor from one site to another. In particular, the language "tumor" is intended to encompass both in vitro and in vivo tumors that form in any organ or body part of the subject. The tumors preferably are tumors sensitive to the Pin1-modulating compounds of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, esophagus, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas (i.e. malignant lymphomas, mantle cell lymphoma), malignant melanomas, multiple myeloma, epidermoid carcinomas, and other carcinomas and sarcomas.

The Pin1 modulating compounds of the present invention may be used to treat, inhibit, and/or prevent undesirable cell growth, neoplasia, and/or cancer in any subject. The Pin1 modulating compounds of the present invention may be used to inhibit Pin1 activity in a subject. In one embodiment, the Pin1 modulating compounds of the present invention may be used to inhibit cyclin D1 expression in a subject.

In one embodiment, the invention pertains, at least in part, to a method for treating a Pin1-associated state in a subject. The method includes administering to a subject an effective amount of a combination of a Pin1 modulating compound of the invention, e.g., Pin1-modulating compounds of formula (I), formula (II), and formula (III), as described above, and a hyperplastic inhibitory agent to treat Pin1 associated disorders.

In another embodiment, the invention pertains, at least in part, to a method for treating cyclin D1 overexpression in a subject. The method includes administering to a subject an effective amount of a combination of a Pin1 modulating compound of the invention, e.g., Pin1-modulating compounds of formula (I), formula (II), and formula (III), as described above, and a hyperplastic inhibitory agent to treat the cyclin D1 overexpression.

In yet another embodiment, the invention pertains, at least in part, to a method for treating cancer in a subject. The method includes administering to a subject an effective amount of a combination of a Pin1 modulating compound of the invention, e.g., Pin1-modulating compounds of formula (I), formula (II), and formula (III), as described above, and a hyperplastic inhibitory agent to treat the cancer.

The language "hyperplastic inhibitory agent" includes agents that inhibit the growth of proliferating cells or tissue wherein the growth of such cells or tissues is undesirable. For example, the inhibition can be of the growth of malignant cells, such as in neoplasms or benign cells, e.g., in tissues where the growth is inappropriate. Examples of the types of agents that can be used include chemotherapeutic agents, radiation therapy treatments, including therapeutically effective ranges of light (e.g., laser light and/or immunofluorescent compounds), and associated radioactive compounds and methods, immunotoxins, and combinations thereof.

The language "chemotherapeutic agent" includes chemical reagents that inhibit the growth of proliferating cells or tissues wherein the growth of such cells or tissues is undesirable. Chemotherapeutic agents are well known in the art (see e.g., Gilman A. G., et al., The Pharmacological Basis of Therapeutics, 8th Ed., Sec 12:1202-1263 (1990)), and are typically used to treat neoplastic disease. Examples of chemotherapeutic agents include: bleomycin, docetaxel (Taxotere), doxorubicin, edatrexate, etoposide, finasteride (Proscar), flutamide (Eulexin), gemcitabine (Gemzar), goserelin acetate (Zoladex), granisetron (Kytril), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), Triapine, vincristine, and vinorelbine tartrate (Navelbine).

In certain embodiments, the chemotherapeutic agent can be, for example, a cancer associated polypeptide inhibitor, e.g., herceptin, or a compound that alters the expression of a cancer associated polypeptide. The use of Pin1 binding compounds in addition to a second anticancer treatment is described in PCT Publication No. WO05027727A2, the contents of which are hereby expressly incorporated by reference in its entirety.

The term "cancer associated polypeptide" refers to a polypeptide whose misexpression has been shown to cause, or be associated with aberrant cell growth, e.g., cancer. Further, cancer associated polypeptides are those that are differentially expressed in cancer cells. In one embodiment, the cancer associated polypeptide is a encoded by an oncogene. In a related embodiment, the cancer associated polypeptide is a polypeptide whose expression has been linked to cancer, e.g., as a marker. The presence of a cancer associated polypeptide can be determined by the presence of the polypeptide or nucleic acid molecules, e.g., mRNA or genomic DNA that encodes the cancer associated polypeptide. Exemplary cancer associated polypeptides include the protein encoded by Her2/neu, (c-erb-2) (Liu et al. (1992) Oncogene 7:1027-32); ras (Nakano, et al. (1984) Proc. Natl. Acad. Sci. U.S.A 81:71-5); Cyclin D1 (Bartkova, et al. (1995) Oncogene 10:775-8, Shamma, et al. (1998) Int. J. Oncol. 13:455-60); E2F1 (Johnson et al. (1994) Proc. Natl. Acad. Sci. 91:12823-7); myc (Corcoran et al. (1984) Cell 37:113-22, Goddard et al. (1986) Nature 322:555-557); jun (Vogt et al. (1990) Adv. Cancer Res. 55:1-35); p53 (Levine et al. (1989) Princess Takamatsu Symp. 20:221-230).

The language "radiation therapy" includes the application of a genetically and somatically safe level of electrons, protons, or photons, both localized and non-localized, to a subject to inhibit, reduce, or prevent symptoms or conditions associated with undesirable cell growth. The term X-rays is also intended to include machine-generated radiation, clinically acceptable radioactive elements, and isotopes thereof, as well as the radioactive emissions therefrom. Examples of the types of emissions include alpha rays, beta rays including hard betas, high-energy electrons, and gamma rays. Radiation therapy is well known in the art (see e.g., Fishbach, F., Laboratory Diagnostic Tests, 3rd Ed., Ch. 10: 581-644 (1988)), and is typically used to treat neoplastic diseases.

The term "immunotoxins" includes immunotherapeutic agents that employ cytotoxic T cells and/or antibodies, e.g., monoclonal, polyclonal, phage antibodies, or fragments thereof, which are utilized in the selective destruction of undesirable rapidly proliferating cells. For example, immunotoxins can include antibody-toxin conjugates (e.g., Abricin and Ab-diphtheria toxin), antibody-radiolabels (e.g., Ab-$I^{135}$) and antibody activation of the complement at the tumor cell. The use of immunotoxins to inhibit, reduce, or prevent symptoms or conditions associated with neoplastic diseases are well known in the art (see, e.g., Harlow, E. and Lane, D., Antibodies, (1988)).

In yet another embodiment, the invention pertains, at least in part, to a method for treating neurodegenerative disease in a subject. The method includes administering to a subject an effective amount of a Pin1 modulating compound of the invention, e.g., Pin1-modulating compounds of formula (I), formula (II), and formula (III), as described above, to treat the neurodegenerative disorder. Exemplary neurodegenerative disorders are Alzheimer's disease, Pick disease, progressive supranuclear palsy, corticobasal degeneration, frontal temporal dementia and parkinsonism linked to chromosome 17.

The invention further provides methods of screening peptides for the ability to bind to a Pin1 polypeptide, or fragment thereof. In one embodiment, the invention provides a method of screening a substrate bound peptide library, e.g., a cellulose bound library, for the ability to bind to Pin1. In one embodiment, a biologically active fragment of Pin1 is used to determine the ability to bind a peptide. In a specific embodiment, the biologically active fragment is a fragment comprising the kinase catalytic domain of Pin1, e.g., residues from about amino acid 51 to about amino acid 153 of human Pin1. To determine which peptides are capable of binding a peptide on the matrix bound library, the library can be incubated with Pin1, or a biologically active fragment thereof, for a time sufficient for binding to occur. The library can then be washed and the matrix can be contacted with a Pin1 specific antibody. The binding of the Pin1 specific antibody can be visualized by the addition of a secondary antibody, as described herein. An exemplary assay to determine the ability of a peptide or peptides from a peptide library to bind to Pin1 is described in the examples.

Pharmaceutical Compositions

The invention also pertains, at least in part, to pharmaceutical compositions of comprising Pin1-modulating compounds of the invention, e.g., Pin1-modulating compounds of (I), formula (II), and formula (III), as described above, and, optionally, a pharmaceutically acceptable carrier.

The language "effective amount" of the compound is that amount necessary or sufficient to treat or prevent a Pin1 associated state, e.g. prevent the various morphological and somatic symptoms of a Pin1 associated state. In an example, an effective amount of the Pin1-modulating compound is the amount sufficient to inhibit undesirable cell growth in a subject. In another example, an effective amount of the Pin1-modulating compound is the amount sufficient to reduce the size of a pre-existing benign cell mass or malignant tumor in a subject. The effective amount can vary depending on such factors as the size and weight of the subject, the type of illness, or the particular Pin1 binding compound. For example, the choice of the Pin1 binding compound can affect what constitutes an "effective amount". One of ordinary skill in the art would be able to study the factors contained herein and make the determination regarding the effective amount of the Pin1 binding compound without undue experimentation. In one possible assay, an effective amount of a Pin1-modulating compound can be determined by assaying for the expression of cyclin D1 and determining the amount of the Pin1-modulating compound sufficient to modulate, e.g., reduce, the levels of cyclin D1 to that associated with a non-cancerous state.

The regimen of administration can affect what constitutes an effective amount. The Pin1 binding compound can be administered to the subject either prior to or after the onset of a Pin1 associated state. Further, several divided dosages, as well as staggered dosages, can be administered daily or sequentially, or the dose can be continuously infused, or can be a bolus injection. Further, the dosages of the Pin1 binding compound(s) can be proportionally increased or decreased as indicated by the exigencies of the therapeutic or prophylactic situation.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats an Pin1 associated state.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

In one embodiment, the invention includes a packaged Pin1-associated state treatment. The packaged treatment includes a Pin1 modulating compound of the invention, e.g., Pin1-modulating compounds of formula (I), formula (II), and formula (III), as described above, packaged with instructions for using an effective amount of the Pin1 modulating compound.

In another embodiment, the invention includes a packaged cell proliferative disease treatment. This packaged treatment include a Pin1 modulating compound of the invention, e.g., Pin1-modulating compounds of formula (I), formula (II), and formula (III), as described above, packaged with instructions for using an effective amount of the Pin1 modulating compound to modulate, e.g., treat, a cell proliferative disease, e.g., cancer.

In yet another embodiment, the invention also pertains, at least in part to a packaged neurodegenerative disease treatment, which includes a Pin1-modulating compound of the invention, e.g., Pin1-modulating compounds of formula (I), formula (II), and formula (III), as described above, packaged with instructions for using an effective amount of the Pin1-modulating compound to treat a neurodegenerative disease, e.g., Alzheimer's disease.

EXEMPLIFICATION OF THE INVENTION

The invention is further illustrated by the following examples, which should not be construed as further limiting.

I. Methods

A. Synthesis of the Cellulose-Bound Combinatorial Peptide Library

The library was prepared by standard automated spot synthesis (Frank, 1992, Kramer et al., 1994 and 1998) using an Auto-Spot Robot ASP 222 (Gilson). The peptides were attached to the cellulose membrane via the side-chain of the C-terminal glutamic acid by coupling of Fmoc-Glu-OtBu to the amino group of the β-Ala-β-Ala-anchor group of the cellulose.

B. Synthesis of Soluble Peptides

Soluble peptides were synthesized on a Syro II multiple peptide synthesizer (MultiSynTech, Germany) using Fmoc-chemistry SPPS-protocols and PyBOP/HOBT as activation reagent. Only activation of protected Thr and D-Thr derivatives was done by HATU/HAOT. Peptides were purified by preparative reverse phase HPLC. Peptide identity was verified by MALDI-TOF mass spectrometry. Fmoc-D-Thr(PO (OBzl)OH)—OH was synthesized according to the procedure of Vorherr & Bannwarth 1995.

C. Screening of the Cellulose-Bound Combinatorial Peptide Library for Substrate-Like Pin1 Ligands Before screening, the cellulose-bound combinatorial peptide library was washed twice with methanol for 10 min followed by four times washing with binding buffer A (25 mM Hepes buffer, pH 7.5, 150 mM NaCl, 7.2 mM KCl, 2% glycerol, 1 mM DTT). The cellulose-bound combinatorial peptide library was then incubated with the hPin1 PPIase domain (40 nM) in binding buffer A for one hour at 4° C. After four washing steps at 4° C. in binding buffer A, the bound hPin1 PPIase domain was electroblotted from the cellulose-bound combinatorial peptide library to a nitrocellulose membrane in a semidry blotting chamber (Biometra) at 96 mA. As transfer buffer 75 mM Tris/HCl (pH 8.0) was used. The nitrocellulose membrane was then blocked by treatment with 20 mM Tris/HCl buffer (pH 7.5) containing 150 mM NaCl, 0.05% Tween 20 and 3% BSA. Detection was done by incubation of the nitrocellulose membrane with an anti hPin1 PPIase domain antiserum from rabbit as primary antibody. As secondary antibody an anti rabbit specific, horseradish peroxidase-conjugated antibody of goat serum was used (Dianova). Detection was done by a chemiluminescent reaction using the SuperSignal®substrate (Pierce).

D. Far Western Blot Related Analysis of the Binding of Peptide 15 Towards Different hPin1 Variants and its Single Domains GST-hPin1 variants, GST-hPin1 PPIase and GST-hPin1 WW domain were prepared as described previously (Ranganathan et al., 1997, Zhou et al., 2000). GST-hPin1 and its single domains were spotted at increasing amounts onto nitrocellulose membranes. Remaining binding sites were blocked by treatment with binding buffer A containing 5% milk powder. The nitrocellulose membranes were then incubated with a 1 μM solution of peptide 15 (see Table III) or 50 μM solution of its nonphosphorylated derivative in binding buffer A. After three washing steps, the nitrocellulose membranes were incubated with 2 μg/ml of horseradish peroxidase conjugated-streptavidin (Pierce) for 90 min. Specific bound peptide 15 was detected by a chemiluminescent reaction using the SuperSignal® substrate (Pierce).

TABLE III

| Peptide | Sequence | $K_i$(nM) |
|---|---|---|
| 15 | Ac-Lys(N$^\epsilon$-biotinoyl)-Ala-Ala-Bth-Thr(PO$_3$H$_2$)-Pip-Nal-Gln-NH$_2$ (SEQ ID NO: 1) | 183 ± 2[a] |
| 16 | Ac-Lys(N$^\epsilon$-biotinoyl)-Ala-Ala-Bth-D-Thr(PO$_3$H$_2$)-Pip-Nal-Gln-NH$_2$ | 1.2 ± 0.6[c] |
| 17 | Ac-Phe-D-Thr(PO$_3$H$_2$)-Pip-Nal-Gln-NH$_2$ | 28.2 ± 3.6[a]/34.4 ± 1[b] |

For the analysis of the binding of peptide 15 towards different GST-hPin1 variants, indicated amounts of peptide 15 were spotted onto nitrocellulose membranes. Blocking and washing steps were done as described above. The nitrocellulose membranes were incubated with different GST-hPin1 variants (40 nM in binding buffer A). To detect specifically the bound protein, the membranes were incubated with an anti hPin1 PPIase domain antiserum as primary antibody and horseradish peroxidase-conjugated secondary antibody. Visualization was done using the SuperSignal® substrate.

E. PPIase Activity Assay

Protein concentrations were determined using the extinction coefficient $\epsilon_{280}$=21030 M$^{-1}$ cm$^{-1}$ for hPin1, $\epsilon_{280}$=6979 M$^{-1}$ cm$^{-1}$ for the hPin1 PPIase domain, $\epsilon_{280}$=21030 M$^{-1}$ cm$^{-1}$ for XlPin1, $\epsilon_{280}$=8250 M$^{-1}$ cm$^{-1}$ for hPar14 and $\epsilon_{280}$=8250 M$^{-1}$ cm$^{-1}$ for hCyp18. Extinction coefficients were calculated using the program ProtParam Tool at ExPASy (SIB, Switzerland). All measurements were done at 10° C. in 35 mM Hepes buffer (pH 7.8).

F. Protease Free Assay

The determination of the kinetic constants of the cis/trans isomerization within the protease-free system was performed using fluorescence based measurements (Garcia-Echeverria et al., 1993, Zhang et al., 2002) on a Hitachi F-3010 fluorescence spectrophotometer with H-Abz-Ala-Glu-Pro-Phe-NH-Np (SEQ ID NO: 2) as substrate. The substrate stock solution was 12 mM in anhydrous trifluoroethanol/0.55 M LiCl. Measurements were initiated by addition of the substrate (final concentration 10 µM) to a pre-incubated (15 min) mixture of 8.8 nM hPin1 or 7.1 nM XlPin1 and respective inhibitory peptide of desired concentrations. The excitation wavelength was 320 nm (spectral bandwidth 3 nm) and emission was detected at 420 nm (spectral bandwidth 10 nm).

G. Protease Coupled PPIase Assay

PPIase activities were monitored on a Hewlett-Packard 8452A diode array spectrophotometer according to Fischer et al., 1984 and Zhang et al., 2002. The hPar14 PPIase activity was measured with Suc-Ala-Arg-Pro-Phe-NH-Np (SEQ ID NO: 3) (final concentration 75 µM) as substrate and α-chymotrypsin (final concentration 60 µM) as isomer specific protease. PPIase activity of hCyp 18 and FKBP12 were measured using Suc-Ala-Ala-Pro-Phe-NH-Np (SEQ ID NO: 7) as substrate (final concentration 16 µM) and α-chymotrypsin (final concentration 60 µM) as isomer specific protease. PPIase activity of hPin1 was measured with Ac-Ala-Ala-Ser(PO$_3$H$_2$)-Pro-Arg-NH-Np (SEQ ID NO: 4) (final concentration 10 µM) as substrate and trypsin (final concentration 60 µM) as isomer specific protease. Final concentrations of the PPIases were 1.7 µM for hPar14, 4 nM for hPin1, 7 nM for FKBP12 and 9.7 nM for hCyp18. Different concentrations of the inhibitory peptide were applied and preincubated (15 min) with the PPIase prior starting the reaction by adding protease and substrate. Measurements were monitored at 390 nm.

Data analysis was performed by single-exponential nonlinear regression using the SigmaPlot Scientific Graphing System Version 5.00 (Jandel Corp.). The apparent first order rate constant $k_{obs}$ was computed by nonlinear regression of the progress curve obtained for the respective measurement. The rate constant $k_0$ was determined in the absence of Pin1. The first order rate constants $k_{enz}$ was calculated from the equation $k_{enz}=k_{obs}-k_0$. IC$_{50}$ and K$_i$ values were determined by fitting the first order rate constants $k_{enz}$ against the concentration of the inhibitory peptide by nonlinear regression according to Schutkowski et al., 1995 or a model for tight binding inhibitors (Morrison, 1969).

H. Isothermal Titration Calorimetry (ITC)

Calorimetric experiments were performed using a VP-ITC titration calorimeter (MicroCal, Inc, Northampton, Mass.) at 10° C. All solutions were degassed under vacuum prior to use. Solutions of hPin1 and hPin1 PPIase domain were dialyzed against 10 mM Hepes (pH 7.8). The protein concentration in the sample cell was adjusted to 6.5 µM using the same batch of buffer. Protein concentrations were determined as described above. The volume of the protein solution in the sample cell was 1.4 ml. The injection syringe was filled with 300 µl solution of peptide 17 (see table III) (250 µM in the same batch of buffer as used for dialyses). Each titration experiment consisted of a single 1 µl injection followed by 16 identical injections of 5 µl solution of peptide 17.

I. Cell Culture and Preparation of HeLa Cell and *X. laevis* Embryo Lysates

HeLa cells were cultured in Dulbecco's Modified Eagle Medium (DMEM, GibcoBRL) supplemented with 10% fetal calf serum at 37° C. with 5% CO$_2$. To induce mitotic arrest, cells were treated with 0.1 µg/ml nocodazole and were allowed to grow for additional 12 hours. Lysates of unsynchronized or mitotic cells were prepared by treatment of the harvested cells with lysis buffer (25 mM Hepes buffer, pH 7.4, 150 mM NaCl, 7.2 mM KCl, 0.5% NP-40, 2% glycerol, 1 mM DTT) for 30 min at 4° C. followed by sonication and centrifugation at 13000 rpm. Depending on the respective experiment, phosphatase inhibitors (10 mM NaF, 1 mM Na$_3$VO$_4$, 0.5 µM okadaic acid) and protease inhibitors (1 mM EDTA, 1 mM EGTA and protease inhibitor mixture, ROCHE, Germany) were added. *X. laevis* embryos were lysed in lysis buffer (10 µl per embryo) containing phosphatase and protease inhibitors (if not otherwise indicated). After centrifugation at 15000 rpm at 4° C. the supernatants were used for experiments.

J. Mutagenesis, Cloning and Overexpression of Recombinant Proteins

Point mutated variants of V5-tagged hPin1 were generated using the QuikChange® Site-Directed Mutagenesis Kit (Stratagene) and V5-tagged hPin1 in pcDNA 3.1/GS (Invitrogen) as a template. GST-hPin and its variants were constructed according to Zhou et al., 2000.

XlPin1 gene was amplified by RT-PCR from *X. laevis* mRNA using specific oligonucleotides. The hPin1 PPIase domain comprising of amino acid residues Gly45-Glu163 was amplified by PCR using specific oligonucleotides and DNA of (His)$_6$hPin1 as a template (Lu et al., 1996). The amplified gene fragments of XlPin1 and hPin1 PPIase domain were cloned in pGEX-4T-1 (Amersham-Pharmacia) and pET28a (Novagen), respectively. For overexpression of the recombinant GST-fused XlPin1 and the hPin1 PPIase domain in *E. coli*, the constructs were transformed in competent *E. coli* JM109 and *E. coli* BL21(DE3) cells, respectively. Expression was induced by addition of 1 mM IPTG to the growing culture in the exponential phase. Purification of recombinant GST-XlPin1 protein and the subsequent cleavage of the N-terminal GST extension was performed according to the manufacturer's protocol using Glutathione Sepharose4B and thrombin as a protease. Recombinant hPin1 PPIase domain was purified as described by the manufacturer using a Ni-NTA column (Novagen).

Capillary Electrophoresis

Peptide 17 was incubated with HeLa cell lysate for 3 h and analyzed with capillary electrophoresis using UV detection at 220 nm on a P/ACE MDQ (Beckman Coulter, Palo Alto, Calif.) system. Fused-silica capillaries (Polymicro Technologies) of 40 cm length at an operation voltage of 20 kV were used. As references, untreated peptide 17 and its nonphosphorylated derivative were used. The samples were hydrodynamically injected with 3.45 kPa for 10 s. 50 mM sodium phosphate buffer (pH 7.0) was used as separation buffer. The system temperature was kept at 16° C.

K. Pull Down Assays

Peptide 16 (see Table III) was incubated with HeLa cell or *X. laevis* embryo lysate for 1 hour at 4° C. The Peptide 16/Pin1 complex was then extracted from the respective mixture using streptavidin sepharose (Pharmacia). After three washing steps in lysis buffer, SDS-sample buffer was added to the beads. The samples were then heated to 95° C. and analyzed by SDS PAGE. Detection of the extracted Pin1 was done by western blot analysis using an anti hPin1 PPIase domain antiserum as primary antibody and a horseradish peroxidase-conjugated secondary antibody. Visualization was done by a chemiluminescent reaction using the SuperSignal® substrate (Pierce).

L. MPM-2 Competition Assay 1.3 mM of Peptide 17 or its nonphosphorylated derivative were incubated with GST-hPin1 (8 μM) for 2 hours at 4° C. After addition of mitotic HeLa cell lysate, the mixture was incubated for 1 hour at 4° C. under gentle rotation. Subsequently, glutathione sepharose beads were added and the mixture was then incubated for an additional hour. The beads were washed three times with lysis buffer. After addition of SDS-sample buffer the mixture was heated up to 95° C. Following SDS-PAGE, the samples were analyzed by western blot analysis. GST-hPin1 and coextracted MPM-2 antigens were detected using an anti hPin1 PPIase domain antiserum (rabbit) or monoclonal anti MPM-2 antibody (Upstate Biotechnology) from mouse. As secondary antibodies, mouse- or rabbit-specific horseradish peroxidase-conjugated antibodies were used. Visualization was done using the SuperSignal® substrate (Pierce).

M. Microinjection and Immunofluorescence

V5-tagged hPin1 and its variants in pcDNA 3.1/GS, provided by Invitrogen, were used as a template to synthesize the according mRNAs using the mMESSAGE mMACHINE™ T7 Kit (Ambion). For microinjection, the indicated amounts of the respective mRNA were dissolved in diethyl pyrocarbonate-treated water. Peptides were dissolved in phosphate buffered saline.

Microinjection was done into the animal half of *X. laevis* embryos at stage 2 of development. In every case, the injection volume was 10 nl. Immunofluorescence studies of frozen *X. laevis* embryo sections were performed as previously described (Julius et al., 2000). Ten-micrometer cryosections of stage 8 embryos were labelled using a monoclonal anti hPin1 antibody (mouse) followed by incubation with Alexa Fluor 546™-conjugated anti mouse antibody of goat serum (Molecular Probes). For visualization of peptide 16, Oregon Green™ 488 labelled NeutrAvidin biotin-binding protein (Molecular Probes) was used. The nuclei were stained by DAPI. Samples were analyzed using an Axioplan epifluorescence microscope with fluorescein and Cy3 selective filter sets. Digital imaging was done using a 768×576 3CCD color video camera (Sony Corp., Tokyo, Japan). Merging of images was performed in Adobe PhotoShop (Adobe Systems Inc., San Jose, Calif.).

II. Results

A. Screening of a Peptide Library for Substrate-Like Pin1 Ligands

To elucidate the mode of action of Pin1 in vivo, tight binding inhibitors associated with Pin1 specificity and metabolic stability has been developed on the basis of oligopeptides. For screening experiments with cellulose-bound phosphopeptides, potential specificity problems associated with the known phosphopeptide affinity of the type IV substrate WW domain were avoided by using the recombinant hPin1 catalytic domain in isolation.

1000 cellulose-bound oligopeptides were screened derived from the known substrate recognition preferences of the catalytic site of hPin1 (Ranganathan et al., 1997, Yaffe et al., 1997).

The compound scans were composed of 5-mer N-acetylated peptides which conform to the general structure Ac-Xaa-Thr($PO_3H_2$)-Yaa-Zaa-NHCH(($CH_2$)$_2$CONH-linker)COOH, containing part of the signature sequence of hPin1 substrates, the aliphatic phosphoester moiety, at an invariant position. The invariant side chain N-alkylated glutamine residue originates from side chain condensation of glutamic acid via the free amino group of matrix-bound β-alanyl-β-alanine linker. Utilizing 9 unnatural hydrophobic amino acids for Zaa and Xaa, and 8 N-alkyl amino acids including L-proline for replacements in position Yaa (Table I) proteolytic stability and hPin1 binding could be manipulated simultaneously. Furthermore, 4-aminomethyl-cyclohexane-carboxylic acid and 4-aminomethyl-benzoic acid were included for substitution in position Yaa to get an idea whether secondary amide bonds formed by an aminomethyl group attached to a six-membered ring can fit into the proline binding pocket of hPin1. The resulting combinatorial cellulose-bound peptide library was screened by incubation with recombinant hPin1 catalytic domain to equilibrium. hPin1 PPIase domain specifically bound to defined peptide spots was visualized using a polyclonal anti hPin1 PPIase domain antiserum (FIG. 1A). In the presence of the Thr($PO_3H_2$)-Yaa moiety (Yaa=any N-alkyl amino acid, 4-aminomethyl-benzoic acid, 4-aminomethyl-cyclohexane-carboxylic acid) exceptional sensitivity to hPin1 PPIase domain binding mapped to position Zaa whereas the whole spectrum of the hydrophobic amino acid derivatives is accepted in position Xaa. The position of Zaa does not tolerate α-t-butyl-glycine, α,α-dibutyl-glycine and 2-aminobenzoic acid but prefers β-(4-biphenylyl)-alanine, β-(3-benzothienyl)-alanine and β-(2-naphtyl)-alanine for hPin1 PPIase domain binding.

It was suggested that the results obtained with the cellulose-bound peptides correlate with the inhibitory power of a corresponding peptide in solution if the Gln residue substitutes for the side-chain anchored glutamic acid.

To reveal whether that correlation holds over a broad distribution of separate spots, a number of strong and weak binders of the library were synthesized in solution by solid phase peptide synthesis (SPPS). A modified version of the cellulose-bound oligopeptide yielded a total of 15 compounds of the general structure Ac-Lys($N^E$-biotinoyl)-Ala-Ala-Xaa-Thr($PO_3H_2$)-Yaa-Zaa-Gln-NH$_2$ (SEQ ID NO: 8) (Table II). The N-terminal extension converts the hPin1 PPIase domain binding peptides of the cellulose-bound library to biotin-labelled molecules that allow pull down experiments with streptavidin coated beads. Obviously this modification does not impede the inhibition of hPin1 PPIase activity.

The determination of $IC_{50}$ values for the blockade of the PPIase activity of hPin1 in the protease free PPIase assay (Garcia-Echeverria et al., 1993, Zhang et al., 2002) verified that the soluble peptides exhibited an inhibitory potency to full-length hPin1 that roughly parallels the emergence of hPin1 PPIase domain binding visualized for the respective spot on the cellulose membrane (FIG. 1 and Table II). The protease free assay ensures reliable measurement of $IC_{50}$ values for the full-length hPin1.

The lowest $IC_{50}$ value of about 200 nM was found for peptide 15 which contains a piperidine-2-carboxylic acid at position Yaa. A prolyl residue at this position (peptide 4) caused a 100 fold decrease of inhibition indicating a tightly regulated active site geometry of hPin1 at P1' position of the substrate-like inhibitor. The peptide 15 at 25 μM concentration does not show any hPin1 inhibition when the phosphoester group on threonine is lacking.

Full-length hPin1 exhibits a dual localization of phosphopeptide-binding sites, and thus provides the potential for the formation of complexes of 2:1 molar stoichiometry. Using domain constructs, a far western blot related assay is able to indicate whether the hPin1 binders additionally affect the WW domain. GST-hPin1, GST-hPin1 PPIase and GST-hPin1 WW domain, respectively, were spotted onto nitrocellulose membranes and incubated with the peptide 15. Specifically bound peptide 15 was then detected using horseradish peroxidase-conjugated streptavidin. FIG. 2A documents that peptide 15 binds only to the PPIase domain of full-length GST-hPin1. Expectedly, full length GST-hPin1 and the GST-hPin1 PPIase domain exhibit similar affinities whereas the peptide lacking the phosphate group was not able to form a complex with GST-hPin1.

The same analysis was performed for GST-hPin1 variants containing mutations within the PPIase domain to identify the side chains of hPin1 responsible for dictating the affinity for peptide 15 and the WW domain variant Ser16Glu (FIG. 2B).

Figure 3:
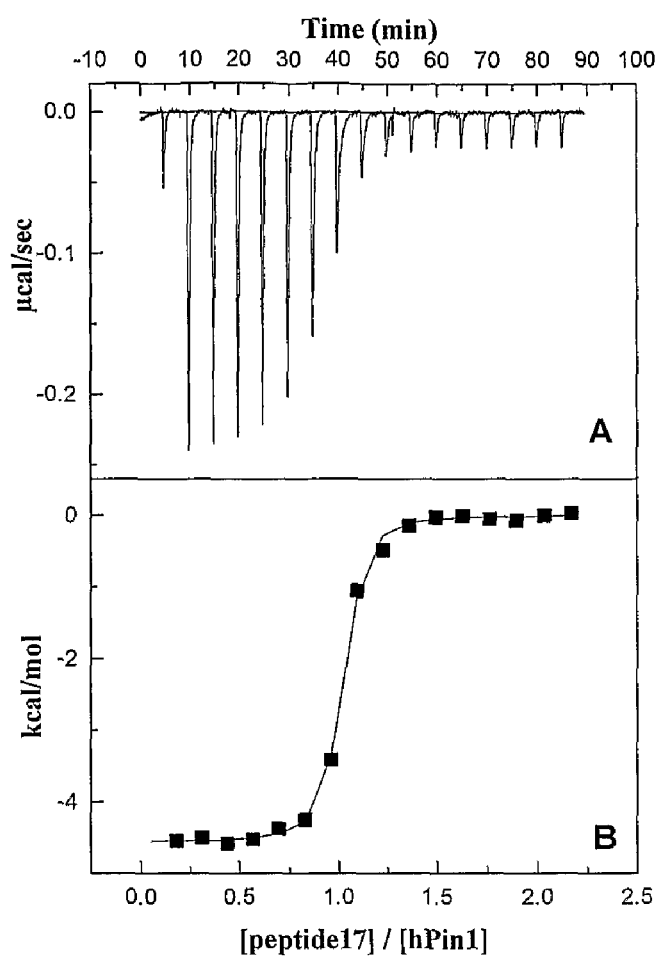
FIGS. 3A-B depicts a thermodynamic characterization of the binding of peptide 17 towards full length hPin1 by isothermal titration calorimetry (ITC).

In principle, minimally four forms of a competing substrate in the presence of hPin1 have to be considered, the free cis and trans isomers together with two Michaelis complexes. This four-site exchange model of PPIase catalysis involves understanding predisposing factors of the stability of hPin1/substrate complexes, expected to be weaker, than the stability for those formed by phosphopeptides lacking substrate properties. The consequent increase in inhibitory potency could be realized by a transition state destabilizing substitution in peptide 15. Previous studies have shown that following $C^\alpha$-stereocenter inversion of a substrate at the P1 position the parvulins fully retain substrate-like active site affinity for the derivatives while catalytic rate acceleration is abolished (Schiene et al., 1998). Thus, a D-Thr(PO$_3$H$_2$) residue at P1 position in peptide 15, which is realized in peptide 16, proved to be useful as an inactivating substitution for the catalytic interconversion of the hPin1-bound peptide. Consequently, the $K_i$ value decreases about 150 fold for peptide 16 approaching the low nanomolar level (Table III). To optimize solute diffusion after mechanical injection of the Pin1 binding peptides into the viscous *Xenopus laevis* egg cytosol, the molecular weight of 1376.5 for peptide 16 was reduced to 823.8 for peptide 17. Following chain truncation peptide 17 maintained high affinity for Pin1 (Table III). To ensure domain selectivity, the binding of peptide 17 towards hPin1 was characterized using the isothermal titration calorimetry (ITC). The analysis of the ITC-titration curve revealed a dissociation constant of $K_D$=19.3±2.6 nM, a binding enthalpy $\Delta H_{bind}$=−4561±36 cal/mol and a binding entropy of $T\Delta S_{bind}$=5433±529 cal/mol (FIGS. 3A, B). The dissociation constant determined with ITC is in the same range as obtained in the protease-free PPIase assay (Table III).

Figure 2:
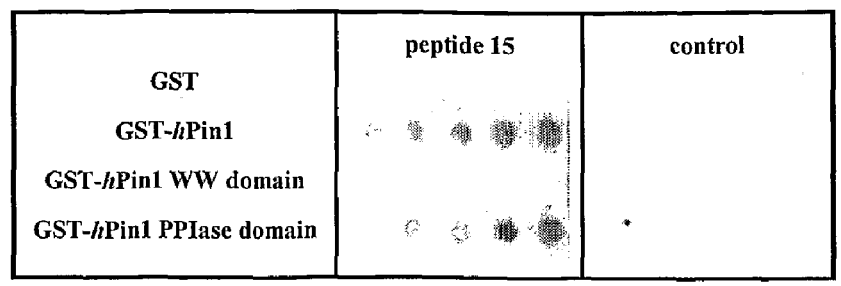
FIGS. 2A-B depict western blot experiments analyzing the binding of peptide 15 to Pin1.
Figure 2:
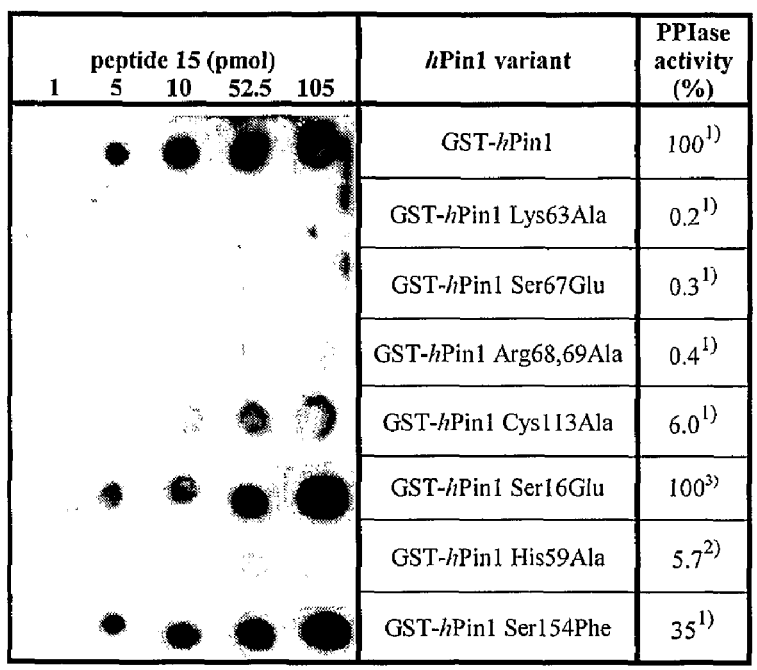

The titration curves demonstrated that peptide 17 only forms an active site complex with full-length hPin1 with a 1:1 stoichiometry confirming similar findings in far western blot analyses with peptide 15 (FIG. 2). Furthermore, the titration of the isolated PPIase domain of hPin1 with peptide 17 gives the same thermodynamic constants as found for titration of full-length hPin1. These results importantly show that stereo-inversion at P1 position of the phosphopeptides does not abolish discrimination against the WW domain. The stability of peptides 15 and 17 in cytoplasmic extracts from HeLa cells was investigated using MALDI-TOF mass spectrometry and capillary electrophoresis, respectively. In the cytosolic incubation mixture, streptavidin sepharose beads served to isolate peptide 15 fragments after prolonged incubation. Analysis of biotinylated degradation products showed that sequence integrity was maintained but the phosphothreonine residues was completely dephosphorylated in the cytosol. The reaction products are inactive toward Pin1. Therefore, phosphopeptides are useless for evaluating Pin1 functions in vivo unless dephosphorylation can be avoided.

Figure 4:
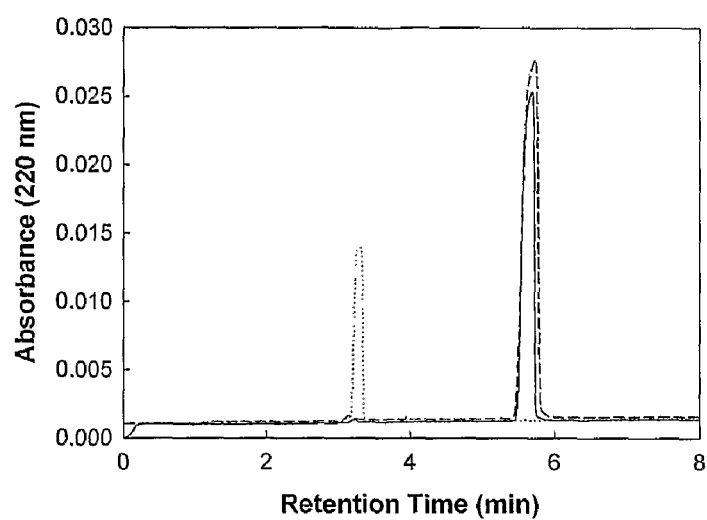
FIG. 4 depicts the stability of peptide 17 against cellular phosphatases and proteases. Peptide 17 was incubated for 3 hours in HeLa cell lysate in the absence of phosphatase and protease inhibitors. The mixture was then analyzed by capillary electrophoresis (short dashed line). As controls, the untreated peptide 17 (solid line) and its nonphosphorylated derivative (dotted line) were used. The temperature of the capillary thermostating system was kept at 16° C. Separation buffer was 50 mM sodium phosphate, pH 7.0. Signals were detected at 220 nm.

It has been reported that the D-Ser(PO$_3$H$_2$) residues in D-Ser(PO$_3$H$_2$)-Pro-peptides confers stability towards cellular phosphatases (Zhang et al., 2002). Consequently, peptide 17 showed complete stability against the HeLa cell lysate after 3 hours of incubation (FIG. 4).

B. Specificity of Inhibition

Peptides 16 and 17 were used for experiments in *Xenopus laevis* embryos. The active site residues of hPin1 that confer affinity for peptides 15-17 are markedly conserved in XlPin1. hPin, which shows 89% sequence identity to XlPin1, is suggested to be a functional replacement for the *Xenopus* enzyme in embryos (Shen et al., 1998), thereby allowing functional replacement. There is no marked difference in affinity of peptide 17 for recombinant Pin1 of both organisms (Table III).

To examine the possibility that peptide 16 could bind to and will inhibit authentic XlPin1 in *X. laevis* embryos, a pull down assay was used. Correspondingly, peptide 16 was incubated with *X. laevis* embryo lysate followed by treatment of the mixture with streptavidin sepharose beads. As shown in FIG. 5A, authentic XlPin1 was coprecipitated with peptide 16 in a dose-dependent manner. Similarly, authentic hPin1 could be pulled down from HeLa cell lysate FIG. 5B.

Figure 6:
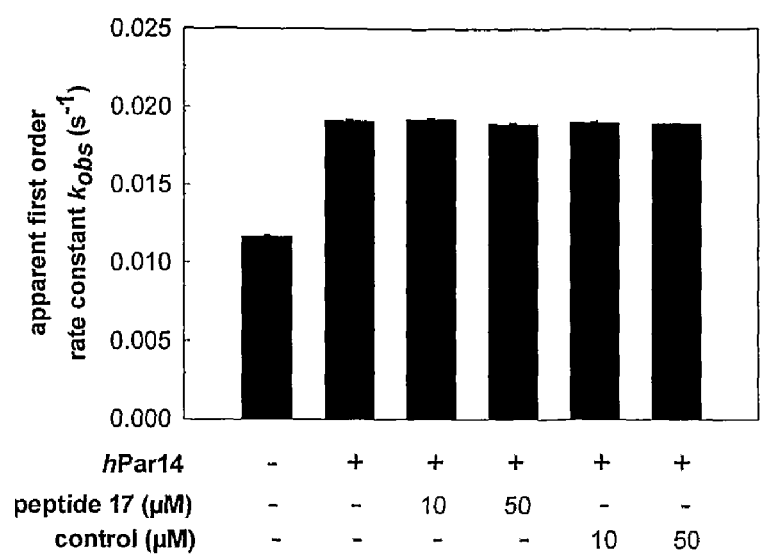
FIG. 6 depicts the influence of peptide 17 on the hPar14 PPIase activity. The apparent first order rate constant $k_{obs}$ determined for the cis to trans isomerization of the arginyl-prolyl peptide bond of the substrate Suc-Ala-Arg-Pro-Phe-NH-Np (SEQ ID NO: 3) was measured using the protease coupled PPIase assay. α-Chymotrypsin was used as isomer specific protease. As control, the nonphosphorylated derivative of peptide 17 was used.

Besides the Pin1, parvulin 14 (hPar14) represents the second PPIase that belongs to the parvulin type family of PPIases in human. Western blotting revealed that antiserum generated against recombinant hPar14 reacted with the 15-kDa component of the *Xenopus* embryo lysate, and the pairwise alignment of a *Xenopus* EST sequence derived protein (Genbank BG578450) and hPar14 gave 75% identity in 128 aa overlap indicating that it is the *Xenopus laevis* counterpart of the Par14. To investigate whether peptide 17 is Pin1 selective, the PPIase activity of hPar14 was examined using a Par14 specific substrate (Uchida et al., 1999) (FIG. 6). No inhibition of hPar14 was observed in the presence of up to 50 µM of peptide 17 or its nonphosphorylated derivative (FIG. 6). Furthermore, no inhibition of Cyp18 and FKBP12 was found.

C. Pin1 Inhibition Does Not Deteriorate MPM-2 Antigen Binding

Figure 7:
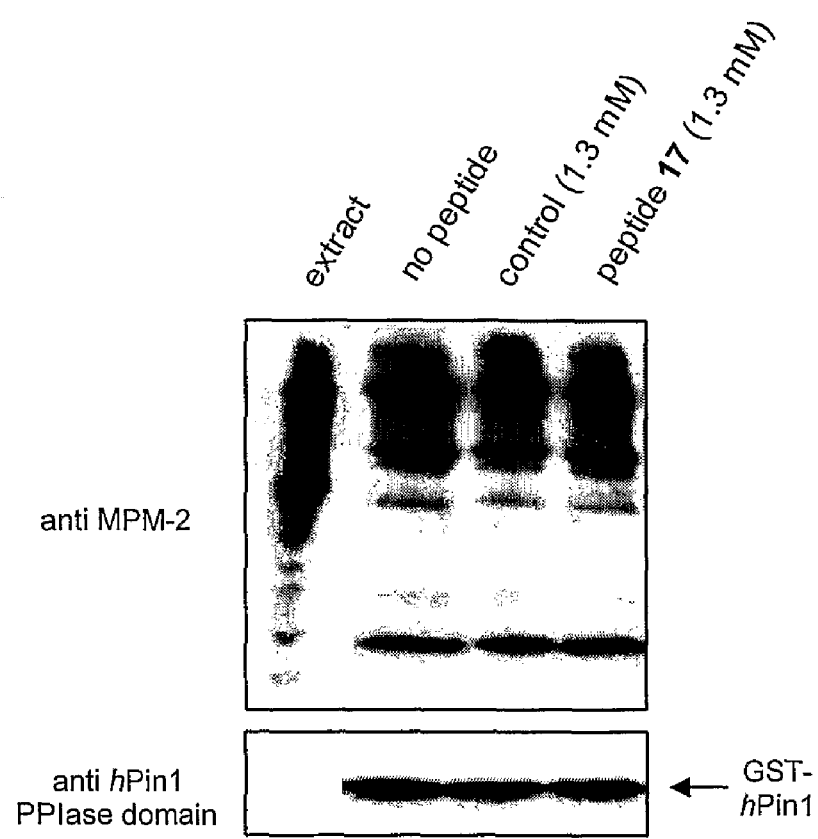
FIG. 7 depicts the influence of peptide 17 on the interaction of MPM-2 antigens with hPin1. The indicated concentration of peptide 17 or its nonphosphorylated derivative (control) was incubated with an 8 µM solution of GST-hPin1. After addition of mitotic HeLa cell lysate, GST-hPin1 was extracted from the respective mixture using glutathione sepharose. Samples were analyzed regarding extracted GST-hPin1 and coprecipitated MPM-2 antigenes by SDS PAGE and western blot analysis. Untreated lysate of mitotic HeLa cells was loaded on the first line (extract). MPM-2 antigens were detected using the monoclonal anti MPM-2 antibody (mouse). GST-hPin1 was detected using an anti hPin1 PPIase domain antiserum (rabbit). Horseradish peroxidase-conjugated antibodies from mouse or rabbit were used as secondary antibodies. Visualization was done using the SuperSignal® substrate.

MPM-2 antigens are mitotic phosphoproteins that are specifically recognized by the monoclonal antibody MPM-2. This antibody is specific for Ser(PO$_3$H$_2$)/Thr(PO$_3$H$_2$)-Pro motifs of these proteins. MPM-2 antigens appear in many proteins that play a crucial role during mitosis, such as Myt1, Wee1, Cdc25, topoisomerase II and Cdc27. It is also known that the biological function of proteins containing MPM-2 antigen motifs may be triggered by interaction with hPin1 (Shen et al., 1998, Zhou et al., 1999 and 2000). From this finding, the question arises whether the binding of peptide 17 to the PPIase domain of full-length hPin1 influences the interaction of MPM-2 antigens with hPin1. In order to answer this question, a MPM-2 competition assay using lysate from mitotic HeLa cells was carried out. HeLa cell lysate from mitotic cells was prepared after induction of cell cycle arrest by nocodazole. GST-hPin1 preincubated with peptide 17 or its nonphosphorylated derivative was then added to the cell lysate. Finally, GST-hPin1 together with bound proteins was extracted from the respective mixture using glutathione sepharose. The coextracted MPM-2 antigenes were detected after SDS PAGE by western blot analysis using the anti MPM-2 antibody. As shown in FIG. 7, peptide 17 did not influence the interaction of the MPM-2 antigenes with GST-hPin1. This result suggests, that peptide 17 inhibits exclusively the PPIase activity without influencing other properties of hPin1. The addition of the nonphosphorylated derivative of peptide 17 had no effect on the interaction of the MPM-2 antigens with GST-hPin1.

Figure 8:
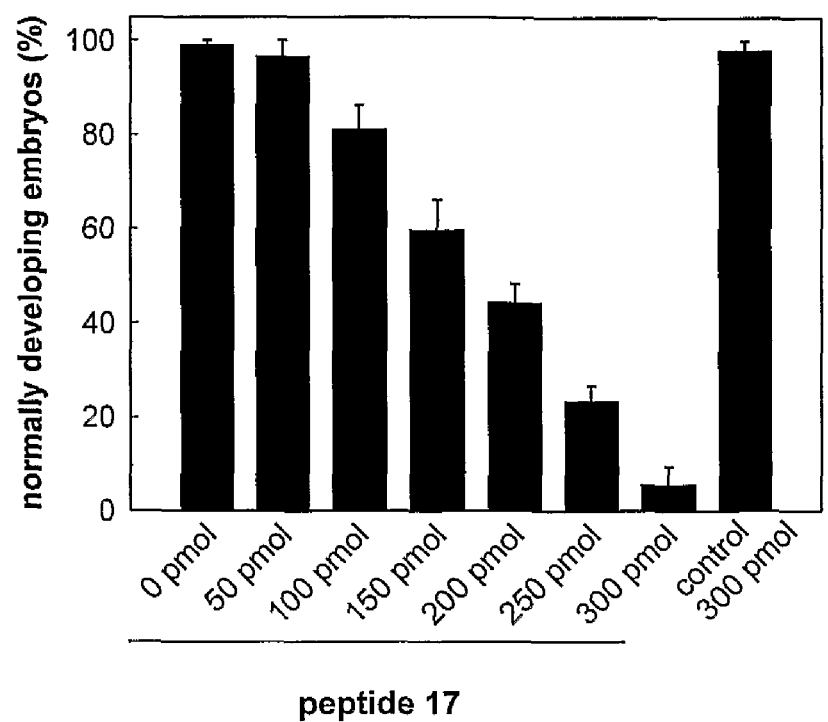
FIG. 8 depicts the blocking of cell division by the injection of peptide 17 in *X. laevis* embryos. 50-300 pmol of peptide 17 or 300 pmol of its nonphosphorylated derivative (control) dissolved in 10 nl PBS buffer were microinjected in the animal half of *X. laevis* embryos at stage 2 of development. Embryos with large and/or apoptotic appearing cells surrounded by normally developing cells were counted after further 5 hours (stage 8-9) of development. The number of vital embryos that did not show any special phenotypic features after injection of peptide 17 is shown in percent relatively to the 30 embryos used per experiment. Each value is the average of four independent experiments.
Figure 9:
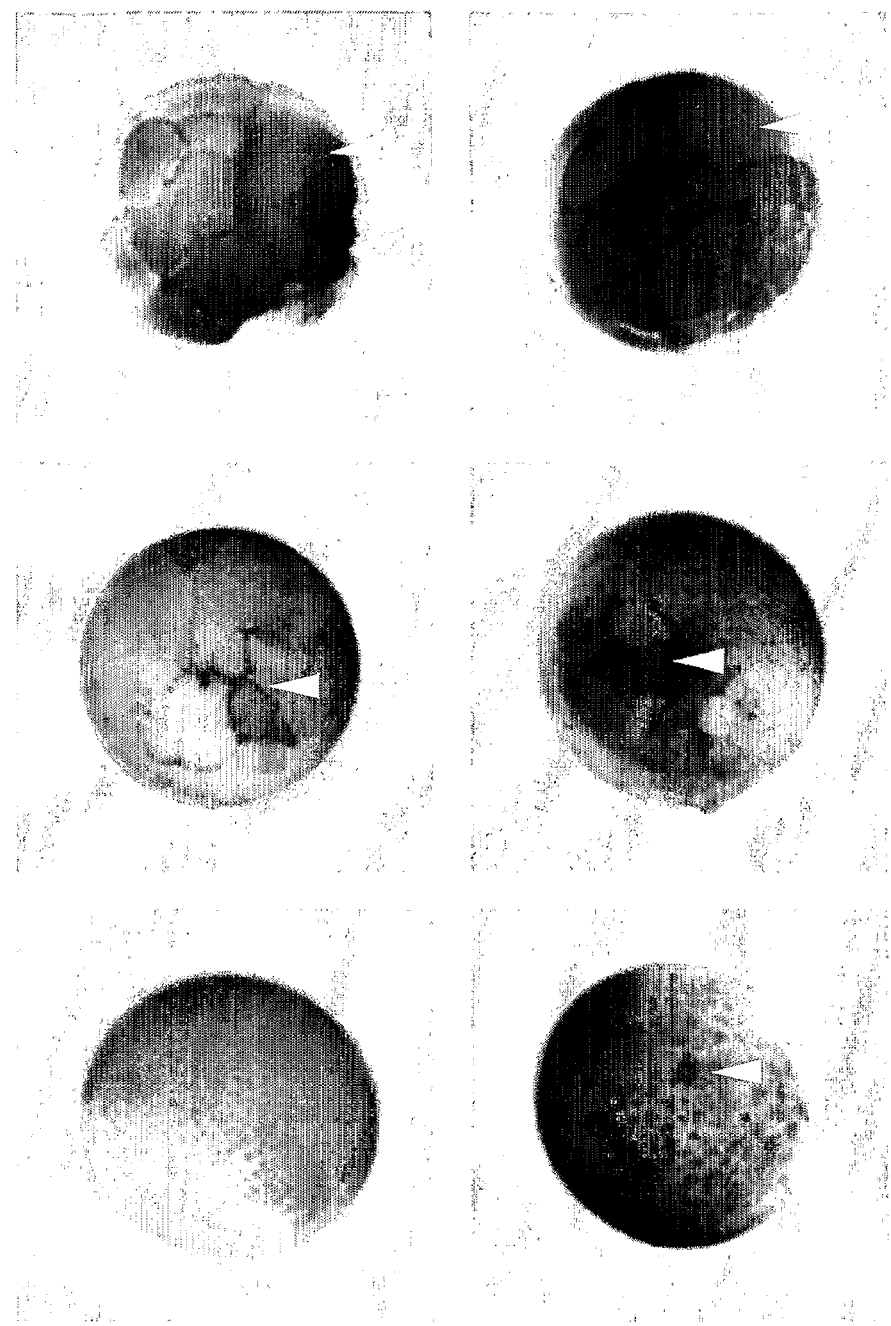
FIGS. 9A-F depicts phenotypic analysis of *X. laevis* embryos after injection of peptide 17. 300 pmol of peptide 17 or its nonphosphorylated derivative dissolved in 10 nl PBS buffer were injected in the animal half of *X. laevis* embryos at stage 2 of development. 1.5 hour at stage 6 (A), 2.5 hours at stage 7 (B) and 4-5 hours at stage 8-9 (C, D) after injection enlarged cells became visible. Cells that are blocked in cell division are marked with a white arrow. Controls of uninjected embryos of stage 8-9 and embryos that were injected with 300 pmol of the nonphosphorylated derivative of peptide 17 are shown in panels E and F. The site where the nonphosphorylated derivative of peptide 17 was injected is marked with a white arrow (F).

D. Cell Division Blockade by Peptide 17 Disturbs the Development of *Xenopus laevis* Embryos With regard to what other Pin1 inhibitors might bring about in in vivo experiments, phosphopeptides display a preference. These compounds block Pin1 PPIase activity separate from WW domain mediated phosphoprotein complexation, taking additional advantage of their unprecedented Pin1 specificity and inhibitory potency. The major drawback in their use is their inability to cross the membrane. Thus, early embryonic development of *Xenopus laevis* was chosen for cell division studies because microinjection into *X. laevis* embryos seems routine (Dawid & Sargent, 1988; Dunphy & Newport, 1988; Guille, 1999). To determine whether peptide 17 influences cell division, different doses of 50 to 300 pmol of the compound dissolved in 10 nl phosphate buffered saline were microinjected in the animal pole of stage 2 *X. laevis* embryos. The phenotype of the embryos was examined 5 hours after injection at stage 8-9 of development. As shown in FIG. 8, the number of embryos with defects in cell division increased at higher doses of peptide 17 achieving a very low number of normal embryos at 300 pmol doses. Visualization of the embryos at stage 6 to 9 revealed the appearance of large cells near the injection side surrounded by normal cells of smaller size (FIGS. 9A, B). The appearance of large cells might indicate continuous mitotic progression for 2-3 further division cycles after injection. The affected cells became apoptotic in later developmental stages (stage 8-9) leading to embryonic death before gastrulation (FIGS. 9C, D). Injection of the nonphosphorylated derivative of peptide 17 as a control had no visible effect on the development of the embryos (FIG. 8, FIGS. 9E, F).

Figure 10A:
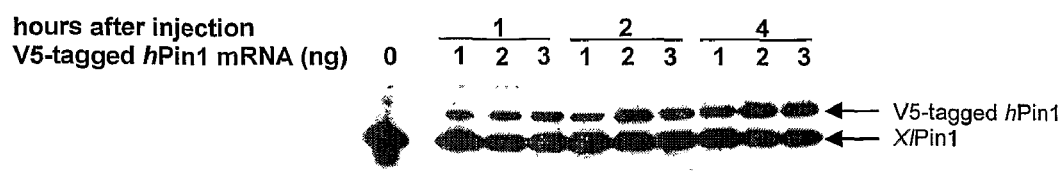
FIGS. 10A-D depict the rescue of peptide 17 caused cell division block in *X. laevis* embryos by hPin1 (A, B) and different hPin1 variants (C, D).
Figure 10B:
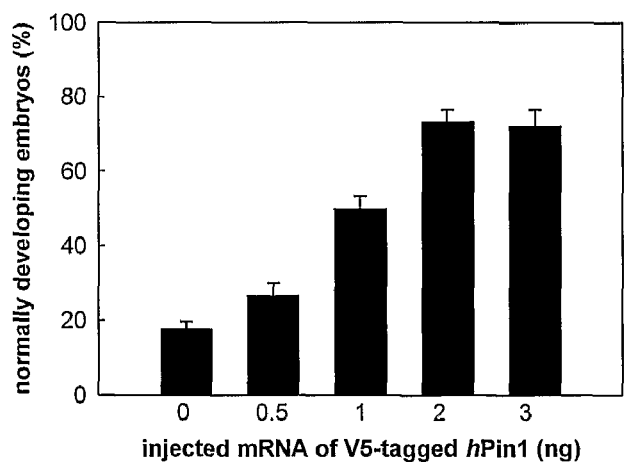

To examine whether the observed effects on *X. laevis* embryonic development are the consequences of a selective inhibition of XlPin1, a rescue experiment was performed by coinjecting peptide 17 and mRNA of V5-tagged hPin1. In a preliminary experiment the time course of V5-tagged hPin1 expression after injection of its mRNA was evaluated. For this purpose, increasing amounts of V5-tagged hPin1 mRNA were injected in stage 2 embryos. Embryo lysates were prepared 1, 2 and 4 hours after injection and analyzed regarding V5-tagged hPin1 expression by western blot analysis (FIG. 10A). Injection of 1 ng mRNA gave a signal of translated V5-tagged hPin1 in only 1 hour time, and XlPin1 provided maternally was present as well. To rescue the cell division block, 250 pmol of peptide 17 were coinjected with different doses of 0-3 ng mRNA of V5-tagged hPin1 in embryos at stage 2 of development. After a postinjection phase of 5 hours, the embryonic phenotypes were analyzed microscopically at stage 8-9. As shown in FIG. 10B, the coexpression of increasing amounts of V5-tagged hPin1 markedly decreased the percentage of embryos with defects in cell cleavage and development. In comparison to control embryos the number of vital embryos increased from 18% without coinjection of mRNA to up to 73% by coinjection of 2 ng of V5-tagged hPin1 mRNA.

Figure 10C:
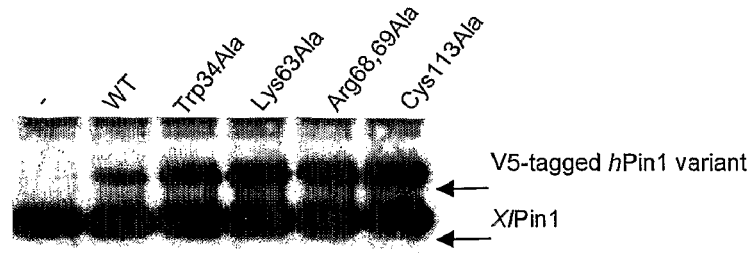
Figure 10D:
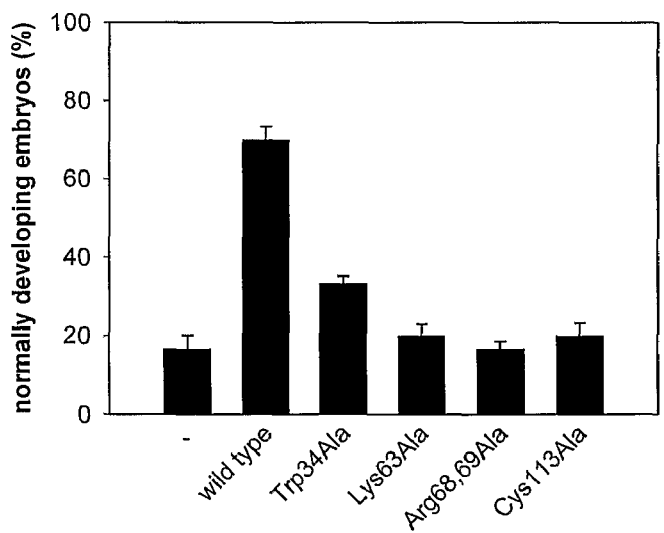

To investigate, whether the capacity of V5-tagged hPin1 to rescue embryos is restricted to the expression of enzymatic activity, mRNAs of different V5-tagged hPin1 variants were used in the coinjection experiments. Expression of the respective mRNA was analyzed in embryo lysates 4 hours after injection by western blot analysis (FIG. 10C). The Lys63Ala, Arg68,69Ala and Cys113Ala variants of V5-tagged hPin1, which are characterized by strongly reduced PPIase activity, could not rescue the peptide 17 caused damages in embryonic development (FIG. 10D). On the contrary, the wild type V5-tagged hPin1 and the V5-tagged hPin1 Trp34Ala variant, which has a substitution in the signature sequence of the WW domain, rescued embryonic development partially after coinjection of its mRNA's.

E. Cellular Distribution of Microinjected Peptide 16

Figure 11:
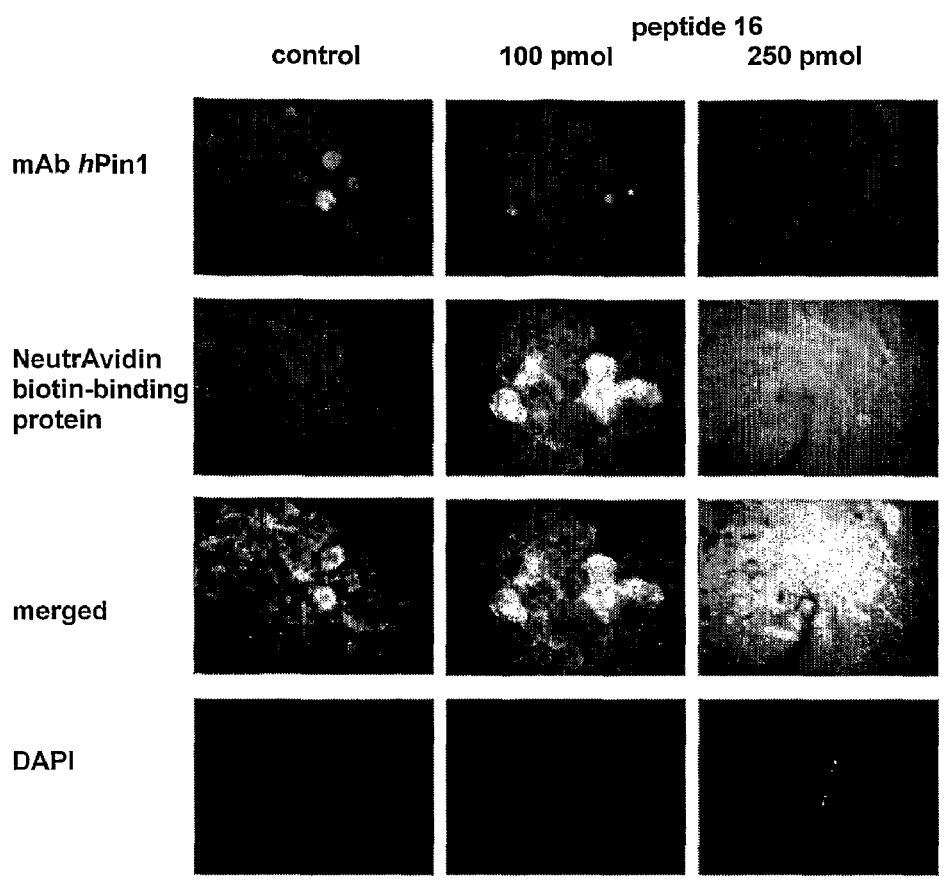
FIG. 11 depicts the colocalization of peptide 16 and endogenous XlPin1 in *X. laevis* embryos. 100 pmol and 250 pmol of peptide 16 dissolved in 10 nl PBS buffer were injected in *X. laevis* embryos at stage 2 of development. In a control experiment, 10 nl of the pure PBS buffer were injected. Embryos were fixed at stage 8, embedded and cryosectioned. Peptide 16 is stained in green using the Oregon Green™ 488-labeled NeutrAvidin biotin-binding protein. Endogenous XlPin1 is stained in red using a monoclonal anti hPin1 antibody (mAb hPin1) from mouse and an Alexa Fluor 546™-conjugated secondary antibody. Overlapping patterns are shown in yellow in the merged images. Nuclei are stained with DAPI.

The biotinoyl label on peptide 16 renders it detectable in the free and XlPin1 bound state within the cell. Thus, localization of peptide 16 in *X. laevis* embryos and the cellular distribution of XlPin1 could be simultaneously assessed by immunofluorescence during development. Embryos at stage 2 of development were injected with 100 or 250 pmol of peptide 16. Fixation of the embryos was done after additional 4 hours of development (stage 8). After cryosection, embryonic tissues were stained using the Oregon Green™ 488-labeled NeutrAvidin biotin-binding protein for detection of peptide 16. Localization of XlPin1 was analyzed in parallel using a monoclonal anti hPin1 antibody followed by treatment with an anti mouse Alexa Fluor 546™-conjugated secondary antibody (FIG. 11). DAPI was used for staining of the nuclei. XlPin1 shows a nuclear and diffuse cytoplasmic distribution. Although, the NeutrAvidin biotin-binding protein conjugate shows a general background staining in the cytoplasm and at the membrane, a clear nuclear colocalization of peptide 16 with XlPin1 could be observed in embryos injected with low amounts of peptide 16 (100 pmol). Injection of 250 pmol of peptide 16 led to distortions of the embryonic tissue caused by large, abnormal cells with fragmented nuclei.

F. Increased Affinity of Peptides with D-Amino Acid at Position Daa

In order to determine the mechanism responsible for increased binding affinity of certain peptides, Pin1 co-crystals were grown with either Ac-Phe-D-Thr($PO_3H_2$)-Pip-Nal-Gln-$NH_2$ or Ac-Phe-L-Thr($PO_3H_2$)-Pip-Nal-Gln-$NH_2$ (SEQ ID NO: 5) bound in the active site. Inspection of the crystal structures revealed that the carbonyl from the Thr($PO_3H_2$) moiety of Ac-Phe-D-Thr($PO_3H_2$)-Pip-Nal-Gln-$NH_2$ was able to form two hydrogen bonds with Ser154 and Gln131, whereas the same carbonyl from Ac-Phe-L-Thr($PO_3H_2$)-Pip-Nal-Gln-$NH_2$ (SEQ ID NO: 5) was oriented away from Ser154 and Gln131. Further, the D-isomer peptide was able to from an intramolecular hydrogen bond between the carbonyl from the Phe moiety and the backbone amide from the Nal moiety. The formation of these additional bonds by the D isomer when compared to the L isomer explain the 30 fold tighter binding of Ac-Phe-D-Thr($PO_3H_2$)-Pip-Nal-Gln-$NH_2$ when compared to Ac-Phe-L-Thr($PO_3H_2$)-Pip-Nal-Gln-$NH_2$ (SEQ ID NO: 5) (Kd of 19 nM as compared to 600 nM).

III. Discussion

In addition to a number of other peptides, a 5-residue peptide, peptide 17 and, its biotin-labeled 8-residue derivatives, peptides 15 and 16, which potently inhibit hPin1 and XlPin1 are disclosed herein. (Peptides 15, 16 and 17 are set forth in Table III). Inhibition is specific among the prototypic members of human PPIases, and peptides 16 and 17 are sufficiently stable in cytosol (FIG. 4). The high expression level of Pin1 in many human cancer cells makes Pin1 inactivation a promising new target process for cancer treatment (Ryo et al., 2003).

By microinjection into *Xenopus* embryos at developmental stage 2 the Pin1 inhibitory peptides 16 and 17 lead to cell cycle blockage and embryonic death establishing a direct functional link between PPIase activity of Pin1 and cell division.

Microinjection of membrane-impermeable compounds, such as phosphopeptides, RNA, proteins and monoclonal antibodies into *X. laevis* oocytes as well as embryos is routinely used to perform functional in vivo studies. For example, the biological properties of farnesyltransferase inhibitors, which also represent potential candidates for the development of anticancer drugs have been evaluated by co-injection of these compounds with oncogenic Ras in *Xenopus* oocytes (Garcia et al., 1993; Manne et al., 1995). Furthermore, the modulation of the human GABA receptor and the mouse 5-hydroxytryptamine(3A) receptor by cGMP-dependent protein kinase (PKG) and protein kinase C (PKC) could be followed using microinjection of the membrane impermeable compound PKCI, a peptide inhibitor of PKC, and the peptide PKGI specifically inhibiting PKG into *Xenopus* oocytes (Leidenheimer, 1996; Coultrap & Machu, 2002). Injection of a specific Calcium/calmodulin-dependent protein kinase II (CaMKII) inhibitory peptide revealed that CaMKII directly modulates potassium channels (Wang et al., 2002). In the PPIase field hPin1 injection in a concentration 20 fold above the estimated level of endogenous Pin1 in *Xenopus* embryos has already been used to completely block cell cleavage during embryogenesis (Shen et al., 1998).

In the experiments described herein, only co-expression of wild type hPin1 prevents cell division block caused by the peptide 17 in a concentration-dependent manner (FIGS. 8, 10B). The hPin1 variants Lys63Ala, Arg68,69Ala and Cys113Ala with impaired catalytic activity (Yaffe et al., 1997) were not able to rescue defects in cell division (FIG. 10D). These results are consistent with in vitro rescue experiments using the XlPin1 Cys109Ala variant in Pin1-depleted interphase *Xenopus* egg extracts (Winkler et al., 2000). hPin1Trp34Ala, a variant point mutated in the WW domain, which has impaired WW-domain directed binding activity for phosphoproteins partially rescues the defective phenotype. The variant seems to sequester the inhibitory peptide to its unperturbed PPIase site thereby rescuing a proportion of endogenous XlPin1 from inhibitor attack.

Figure 5:
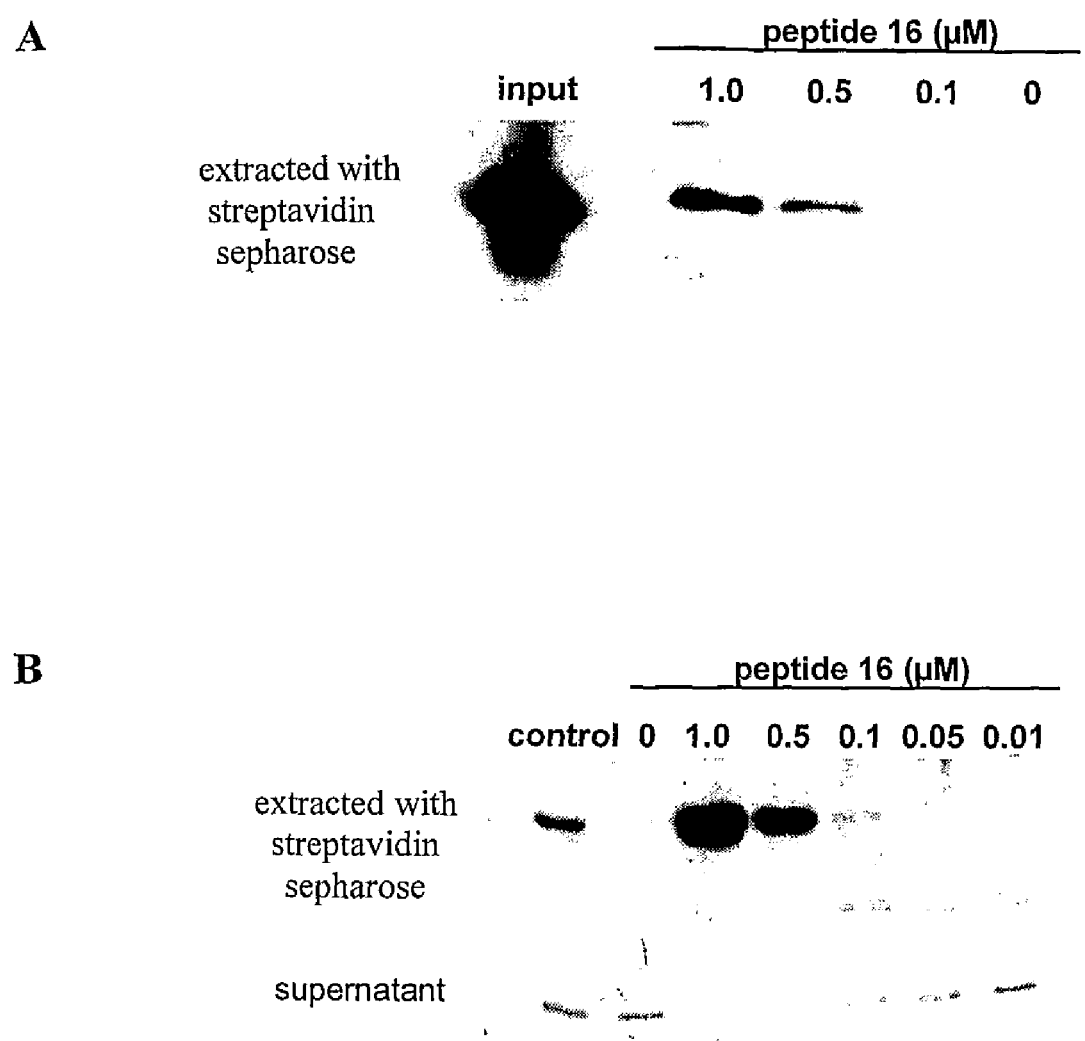
FIGS. 5A-B depict pull down assays showing peptide 16 binds to authentic XlPin1 (A) and hPin1 from HeLa cells (B).

Substrate-like peptide libraries attached to a cellulose matrix are especially suitable as display platforms for active site directed epitopes, which are a guarantee for specific and potent inhibition. The cellulose-bound peptide library of the general sequence Ac-Xaa-Thr($PO_3H_2$)-Yaa-Zaa-NHCH(($CH_2$)$_2$CONH-linker)COOH (SEQ ID NO: 6) was found to be most useful in discriminating between the two phosphopeptide-binding domain within Pin1, the WW domain and the parvulin-like catalytic domain (FIG. 2). In fact, the isothermal titration calorimetry of the hPin1/peptide 17 association showed the exclusive formation of the inhibitory hPin1 complex in a 1:1 stoichiometry. Since the dephosphorylated peptides completely failed in binding to and inhibition of hPin1 inert derivatives analogous to inhibitors became readily available for biological studies (FIGS. 7, 8 and 9F). Structure-activity relationships showed that combinations of substitutions that individually influence the active site affinity produce enhanced inhibition when combined in a single molecule (Table II). To ensure phosphorolytic stability and avid Pin1 binding (Table III) and inversion of the Thr($PO_3H_2$) configuration of peptide 15 was performed since phosphopeptides with a reversed stereocenter at P1 position experiences a mechanism-based gain of stability of their Pin1 complexes (Schiene et al., 1998). For example, the 150 fold higher inhibitory potency of the biotinylated peptide 16 when compared to peptide 15 (Table III) results in an exceptionally potent Pin 1 inhibitor (1.2 nM) that allows extraction of inhibitor-binding proteins by streptavidin pull-down from the cytosol of Hela cells and *Xenopus* egg extracts, and localization of the inhibitory Pin1 complex in the *Xenopus* embryos. Under these conditions the authentic Pin1 was the major protein absorbed to the streptavidin affinity matrix as detected by Western blot analyses (FIG. 5).

Peptide 15/MPM-2 competition experiments in mitotic extracts of Hela cells were used in an attempt to analyze the relative roles of these WW and PPIase domain mediated mechanisms.

In vitro pull down assays confirmed, that the binding of peptide 15 to hPin1 exclusively targets the PPIase domain leaving intact the binding sites of MPM-2 antigenic proteins from mitotic HeLa cell extract on the WW domain. hPin1 binds mitotic phosphoproteins from mitotic HeLa cell as well as mitotic *Xenopus* extract (Shen et al., 1998). A subset of these proteins are also recognized by the monoclonal MPM-2 antibody (Lu et al., 1999b; Crenshaw et al., 1998; Shen et al., 1998; Yaffe et al., 1997). The hPin1 WW domain belongs to group IV WW domains and acts as a specific Ser($PO_3H_2$)/Thr($PO_3H_2$)-Pro binding module thereby mediating interactions with its phosphorylated cellular targets. Phosphorylation of Ser16 in the WW domain has been shown to regulate hPin1 subcellular localization and binding to its phosphoprotein targets (Lu et al., 2002a). However, Ser16Glu substitution in hPin1 had virtually no effect on the affinity of peptide 15 to the enzyme in contrast to the reduced affinity of Pin1 variants with mutations in the PPIase domain (FIG. 2B). Thus, the insignificance of the WW domain properties to cell cycle effects obtained in developing *Xenopus* embryos after exposure to peptide 16 and 17 is quite evident when considering the unperturbed WW domain interacting site in the peptide/Pin1 complexes (FIG. 7).

Immunodepletion of XlPin1 from cycling egg extracts causes premature entry into mitosis accompanied by hyperphosphorylation of Cdc25 and Cdc2/cyclin B activation (Winkler et al., 2000). Similarly, HeLa cells overexpressing hPin1 show an inhibition of the G2/M transition, and hPin1 depletion results in mitotic arrest characterized by chromatin condensation and nuclear lamin disassembly (Lu et al., 1996). These phenotypes correspond to cell division block after microinjection of peptide 17 in *Xenopus* two-cell stage embryos, and must be caused by specifically inhibiting endogenous XlPin1 near the injection site. Microinjection of reference peptides refractory to Pin1 active site binding does not show any effect on embryonic development. Cell division was not blocked immediately after injection, it occurs about 2-3 divisions after injection. This might be explained by the diffusion limitations of the inhibitor in view of the intrinsically fast cell divisions, and cell cycle continuation during injection. Microinjection of a monoclonal antibody against Dnmt1, which represents key enzyme in the maintenance of DNA methylation with a crucial role during early embryogenesis, causes a cell division phenotype of embryos similar to our Pin1 inhibitor (Hashimoto et al., 2003). Similarly, embryos that have been injected at developmental stage 2 started to unveiled their phenotypes after further three cell cycles at stage 5.

Employing the tight interaction between streptavidin and biotin, biotinylated inhibitory peptides are helpful tools to localize enzyme/inhibitor complexes in single cells and tissues as well as to isolate new proteins. As previously demonstrated for hPin1, XlPin1 shows exactly the same distribution pattern in the cell with a distinct localization to the nucleus and a weaker diffuse spreading in the cytoplasm (Lu et al., 1996). The injected biotinylated peptide 16 does not change the cellular distribution of endogenous XlPin1 but clearly co-localizes to the same cellular structures (FIG. 11).

Although individual inhibition of Pin1 seems sufficient for blocking cell division in *Xenopus*, hypotheses about the non-essential character of Pin1 in other organisms remain elusive. Depletion of hPin1 confers mitotic lethality in Hela cells, and ess1 gene deletion in yeast is also lethal. However, for mice and *D. melanogaster* Pin1 is not essential for the viability of the respective organism (Hanes et al., 1989; Lu et al., 1996; Maleszka et al., 1996; Fujimori et al., 1999).

Moreover, expression of the hPin1, XlPin1 or the Pin1 homologue Dodo of *D. melanogaster* fully rescues the lethal phenotype of ess/ptf1 null mutants in yeast (Lu et al., 1996; Maleszka et al., 1996; Winkler et al., 2000). This functional interchangeability of hPin1 homologous proteins from different eukaryotic organisms is based on the high conservation of specific amino acid residues within their sequences giving rise to the suspicion that the homologues participate in the same biochemical pathways within different organisms. The amino acid sequences of XlPin1 and hPin1 share 89% identity with strict conservation of proposed PPIase active site residues.

Previous studies show, that similar to the mitotic regulator hPin1, XlPin1 is required for regulatory steps during the DNA replication checkpoint preventing premature entry into mitosis in response to incomplete DNA replication (Winkler et al., 2000).

REFERENCES

Albert, A., Lavoie, S. and Vincent, M. (1999) A hyperphosphorylated form of RNA polymerase II is the major interphase antigen of the phosphoprotein antibody MPM-2 and interacts with the peptidyl-prolyl isomerase Pin1. *J Cell Sci*, 112, 2493-2500.

Andreotti, A. H. (2003) Native state proline isomerization: An intrinsic molecular switch. *Biochemistry*, 42, 9515-9524.

Atchison, F. W., Capel, B. and Means, A. R. (2003) Pin1 regulates the timing of primordial germ cell proliferation. *Development*, 130, 3579-3585.

Arevalo-Rodriguez, M., Cardenas, M. E., Wu, X., Hanes, S. D. and Heitman, J. (2000) Cyclophilin A and Ess1 interact with and regulate silencing by the Sin3-Rpd3 histone deacetylase. *Embo J*, 19, 3739-3749.

Chao, S. H., Greenleaf, A. L. and Price, D. H. (2001) Juglone, an inhibitor of the peptidyl-prolyl isomerase Pin1, also directly blocks transcription. *Nucleic Acids Res*, 29, 767-773.

Crenshaw, D. G., Yang, J., Means, A. R. and Kornbluth, S. (1998) The mitotic peptidyl-prolyl isomerase, Pin1, interacts with Cdc25 and Plx1. *Embo J*, 17, 1315-1327.

Coultrap, S. J. and Machu, T. K. (2002) Enhancement of 5-hydroxytryptamine3A receptor function by phorbol 12-myristate, 13-acetate is mediated by protein kinase C and tyrosine kinase activity. *Receptors Channels*, 8, 63-70.

Devasahayam, G., Chaturvedi, V. and Hanes, S. D. (2002) The Ess1 prolyl isomerase is required for growth and morphogenetic switching in *Candida albicans*. *Genetics*, 160, 37-48.

Dawid, I. B. and Sargent, T. D. (1988) *Xenopus laevis* in developmental and molecular biology. *Science*, 240, 1443-1448.

Dunphy, W. G. and Newport, J. W. (1988) Unraveling of mitotic control mechanisms. *Cell*, 55, 925-928.

Fischer, G., Bang, H. and Mech, C. (1984) Determination of enzymatic catalysis for the cis-trans-isomerization of peptide binding in proline-containing peptides. *Biomed Biochim Acta*, 43, 1101-1111.

Fischer G. and Aumüller, T. (2003) Regulation of peptide bond cis/trans isomerization by enzyme catalysis and its implication in physiological processes. *Rev Physiol Biochem Phamacol*, 148, 105-150.

Frank, R., (1992) Spot-Synthesis: An easy technique for the positionally addressable, parallel chemical synthesis on a membrane support. *Tetrahedron*, 48, 9217-9232.

Fujimori, F., Takahashi, K., Uchida, C. and Uchida, T. (1999) Mice lacking Pin1 develop normally, but are defective in entering cell cycle from G(0) arrest. *Biochem Biophys Res Commun*, 265, 658-663.

Fujimori, F., Gunji, W., Kikuchi, J., Mogi, T., Ohashi, Y., Makino, T., Oyama, A., Okuhara, K., Uchida, T. and Murakami, Y. (2001) Crosstalk of prolyl isomerases, Pin1/Ess1, and cyclophilin A. *Biochem Biophys Res Commun*, 289, 181-190.

Garcia, A. M., Rowell, C., Ackermann, K., Kowalczyk, J. J. and Lewis, M. D. (1993) Peptidomimetic inhibitors of Ras farnesylation and function in whole cells. *J Biol Chem*, 268, 18415-18418.

Garcia-Echeverria, C., Kofron, J. L., Kuzmic, P., and Rich, D. H. (1993) A continuous spectrophotometric assay for peptidyl prolyl cis-trans isomerases. *Biochem Biophys Res Commun*, 191, 70-75.

Guille, M. (1999) Microinjection into *Xenopus* oocytes and embryos. *Methods Mol Biol.*, 127, 111-123.

Hall, F. L. and Vulliet, P. R. (1991) Proline-directed protein phosphorylation and cell cycle regulation. *Curr Opin Cell Biol*, 3, 176-184.

Hanes, S. D., Shank, P. R. and Bostian, K. A. (1989) Sequence and mutational analysis of ESS1, a gene essential for growth in *Saccharomyces cerevisiae*. *Yeast*, 5, 55-72.

Hani, J., Stumpf, G. and Domdey, H. (1995) PTF1 encodes an essential protein in *Saccharomyces cerevisiae*, which shows strong homology with a new putative family of PPIases. *FEBS Lett*, 365, 198-202.

Hani, J., Schelbert, B., Bernhardt, A., Domdey, H., Fischer, G., Wiebauer, K. and Rahfeld, J. U. (1999) Mutations in a peptidylprolyl-cis/trans-isomerase gene lead to a defect in 3'-end formation of a pre-mRNA in *Saccharomyces cerevisiae*. *J Biol Chem*, 274, 108-116.

Hashimoto, H., Suetake, I. and Tajima, S. (2003) Monoclonal antibody against dnmt1 arrests the cell division of *xenopus* early-stage embryos. *Exp Cell Res*, 286, 252-262.

Hennig, L., Christner, C., Kipping, M., Schelbert, B., Rucknagel, K. P., Grabley, S., Kullertz, G. and Fischer, G. (1998) Selective inactivation of parvulin-like peptidyl-prolyl cis/trans isomerases by juglone. *Biochemistry*, 37, 5953-5960.

Hsu, T., McRackan, D., Vincent, T. S. and Gert de Couet, H. (2001) *Drosophila* Pin1 prolyl isomerase Dodo is a MAP kinase signal responder during oogenesis. *Nat Cell Biol*, 3, 538-543.

Julius, M. A., Schelbert, B., Hsu, W., Fitzpatrick, E., Jho, E., Fagotto, F., Costantini, F. and Kitajewski, J. (2000) Domains of axin and disheveled required for interaction and function in wnt signaling. *Biochem Biophys Res Commun*, 276, 1162-1169.

Kops, O., Eckerskorn, C., Hottenrott, S., Fischer, G., Mi, H. and Tropschug, M. (1998) Ssp1, a site-specific parvulin homolog from *Neurospora crassa* active in protein folding. *J Biol Chem*, 273, 31971-31976.

Kops, O., Zhou, X. Z. and Lu, K. P. (2002) Pin1 modulates the dephosphorylation of the RNA polymerase II C-terminal domain by yeast Fcp1. *FEBS Lett*, 513, 305-311.

Kramer, A., Schuster, A., Reineke, U., Malin, R., Volkmer-Engert, R., Landgraf, C. and Schneider-Mergener, J. (1994) Combinatorial cellulose-bound peptide libraries: screening tool for the identification of peptides that bind ligands with predefined specificity. *Methods Comp Methods Enzymol*, 6, 388-395.

Kramer, A. and Schneider-Mergener, J. (1998) Synthesis and screening of peptide libraries on cellulose membrane supports. *Methods Mol Biol*, 87, 25-39.

Landrieu, I., De Veylder, L., Fruchart, J. S., Odaert, B., Casteels, P., Portetelle, D., Van Montagu, M., Inze, D. and Lippens, G. (2000) The *Arabidopsis thaliana* PIN1At gene encodes a single-domain phosphorylation-dependent peptidyl prolyl cis/trans isomerase. *J Biol Chem*, 275, 10577-10581.

Leidenheimer, N. J. (1996) Effect of PKG activation on recombinant GABA A receptors. *Brain Res Mol Brain Res*, 42, 131-134.

Liou, Y. C., Ryo, A., Huang, H. K., Lu, P. J., Bronson, R., Fujimori, F., Uchida, T., Hunter, T. and Lu, K. P. (2002) Loss of Pin1 function in the mouse causes phenotypes resembling cyclin D1-null phenotypes. *Proc Natl Acad Sci USA*, 99, 1335-1340.

Liu, W. F., Youn, H. D., Zhou, X. Z., Lu, K. P. and Liu, J. O. (2001) Binding and regulation of the transcription factor NFAT by the peptidyl prolyl cis-trans isomerase Pin1. *FEBS Lett*, 496, 105-108.

Lu, K. P., Hanes, S. D. and Hunter, T. (1996) A human peptidyl-prolyl isomerase essential for regulation of mitosis. *Nature*, 380, 544-547.

Lu, P. J., Wulf, G., Zhou, X. Z., Davies, P. and Lu, K. P. (1999a) The prolyl isomerase Pin1 restores the function of Alzheimer-associated phosphorylated tau protein. *Nature*, 399, 784-788.

Lu, P. J., Zhou, X. Z., Shen, M. and Lu, K. P. (1999b) Function of WW domains as phosphoserine- or phosphothreonine-binding modules. *Science*, 283, 1325-1328.

Lu, P. J., Zhou, X. Z., Liou, Y. C., Noel, J. P. and Lu, K. P. (2002a) Critical role of WW domain phosphorylation in regulating phosphoserine binding activity and Pin1 function. *J Biol Chem*, 277, 2381-2384.

Lu, K. P., Liou, Y. C. and Zhou, X. Z. (2002b) Pinning down proline-directed phosphorylation signaling. *Trends Cell Biol*, 12, 164-172.

Lu, K. P., Liou, Y. C. and Vincent, I. (2003) Proline-directed phosphorylation and isomerization in mitotic regulation and in Alzheimer's Disease. *Bioessays*, 25, 174-181.

Maleszka, R., Hanes, S. D., Hackett, R. L., de Couet, H. G. and Miklos, G. L. (1996) The *Drosophila melanogaster* dodo (dod) gene, conserved in humans, is functionally interchangeable with the ESS1 cell division gene of *Saccharomyces cerevisiae*. *Proc Natl Acad Sci USA*, 93, 447-451.

Maleszka, R., Lupas, A., Hanes, S. D. and Miklos, G. L. G. (1997) The DODO gene family encodes a novel protein involved in signal transduction and protein folding. *Gene*, 203, 89-93.

Manne, V., Yan, N., Carboni, J. M., Tuomari, A. V., Ricca, C. S., Brown, J. G., Andahazy, M. L., Schmidt, R. J., Patel, D., Zahler, R. and et al. (1995) Bisubstrate inhibitors of farnesyltransferase: a novel class of specific inhibitors of ras transformed cells. *Oncogene*, 10, 1763-1779.

Metzner, M., Stoller, G., Rucknagel, K. P., Lu, K. P., Fischer, G., Luckner, M. and Küllertz, G. (2001) Functional replacement of the essential ESS1 in yeast by the plant parvulin DlPar13. *J Biol Chem*, 276, 13524-13529.

Morrison, J. F. (1969) Kinetics of the reversible inhibition of enzyme-catalysed reactions by tight-binding inhibitors. *Biochim Biophys Acta*, 185, 269-286.

Myers, J. K., Morris, D. P., Greenleaf, A. L. and Oas, T. G. (2001) Phosphorylation of RNA polymerase II CTD fragments results in tight binding to the WW domain from the yeast prolyl isomerase Ess1. *Biochemistry*, 40, 8479-8486.

Ng, K. K. and Weis, W. I. (1998) Coupling of prolyl peptide bond isomerization and Ca2+ binding in a C-type mannose-binding protein. *Biochemistry*, 37, 17977-17989.

Nishinakamura, R., Matsumoto, Y., Uochi, T., Asashima, M. and Yokota, T. (1997) *Xenopus* FK 506-binding protein homolog induces a secondary axis in frog embryos, which is inhibited by coexisting BMP 4 signaling. *Biochem Biophys Res Commun*, 239, 585-591.

Pappenberger, G., Bachmann, A., Müller, R., Aygün, H., Engels, J. W. and Kiefhaber, T. (2003) Kinetic mechanism and catalysis of a native-state prolyl isomerization reaction. *J Mol Biol*, 336, 235-246.

Pearson, G., Robinson, F., Gibson, T. B., Xu, B. E., Karandikar, M., Berman, K. and Cobb, M. H. (2001) Mitogen-activated protein (MAP) kinase pathways: Regulation and physiological functions. *Endocr. Rev.*, 22, 153-183.

Ranganathan, R., Lu, K. P., Hunter, T. and Noel, J. P. (1997) Structural and functional analysis of the mitotic rotamase Pin1 suggests substrate recognition is phosphorylation dependent. *Cell*, 89, 875-886.

Reimer, U. and Fischer, G. (2002) Local structural changes caused by peptidyl-prolyl cis/trans isomerization in the native state of proteins. *Biophys Chem*, 96, 203-212.

Rippmann, J. F., Hobbie, S., Daiber, C., Guilliard, B., Bauer, M., Birk, J., Nar, H., Garin-Chesa, P., Rettig, W. J. and Schnapp, A. (2000) Phosphorylation-dependent proline isomerization catalyzed by Pin1 is essential for tumor cell survival and entry into mitosis. *Cell Growth Differ*, 11, 409-416.

Rulten, S., Thorpe, J., and Kay, J. (1999). Identification of eukaryotic parvulin homologues: A new subfamily of peptidylprolyl cis/trans isomerases. *Biochim Biophys Res Commun*, 259, 557-562

Ryo, A., Nakamura, M., Wulf, G., Liou, Y. C. and Lu, K. P. (2001) Pin1 regulates turnover and subcellular localization of beta-catenin by inhibiting its interaction with APC. *Nat Cell Biol*, 3, 793-801.

Ryo, A., Liou, Y. C., Wulf, G., Nakamura, M., Lee, S. W. and Lu, K. P. (2002) PIN1 is an E2F target gene essential for Neu/Ras-induced transformation of mammary epithelial cells. *Mol Cell Biol*, 22, 5281-5295.

Ryo, A., Liou, Y. C., Lu, K. P. and Wulf, G. (2003) Prolyl isomerase Pin1: a catalyst for oncogenesis and a potential therapeutic target in cancer. *J Cell Sci*, 116, 773-783.

Schiene, C., Reimer, U., Schutkowski, M. and Fischer, G. (1998) Mapping the stereospecificity of peptidyl prolyl cis/trans isomerases. *FEBS Lett*, 432, 202-206.

Schutkowski, M., Wöllner, S., Fischer, G. (1995) Inhibition of peptidyl-prolyl cis/trans isomerase activity by substrate analogue structures: thioxo tetrapeptide-4-nitroanilids. *Biochemistry*, 34, 13016-13026.

Shaw, P. E. (2002) Peptidyl-prolyl isomerases: a new twist to transcription. *EMBO Rep*, 3, 521-526.

Shen, M. H., Stukenberg, P. T., Kirschner, M. W. and Lu, K. P. (1998) The essential mitotic peptidyl-prolyl isomerase Pin1 binds and regulates mitosis-specific phosphoproteins. *Genes Dev*, 12, 706-720.

Spokony, R. and Saint-Jeannet, J. P. (2000) *Xenopus* FK 506-binding protein, a novel immunophilin expressed during early development. *Mech Dev*, 94, 205-208.

Stockwell, B. R., Haggarty, S. J. and Schreiber, S. L. (1999) High-throughput screening of small molecules in miniaturized mammalian cell-based assays involving post-translational modifications. *Chem Biol*, 6, 71-83.

Thorpe, J. R., Morley, S. J. and Rulten, S. L. (2001) Utilizing the peptidyl-prolyl cis-trans isomerase Pin1 as a probe of its phosphorylated target proteins: Examples of binding to nuclear proteins in a human kidney cell line and to tau in Alzheimer's diseased brain. *J Histochem Cytochem*, 49, 97-107.

Uchida, T., Fujimori, F., Tradler, T., Fischer, G. and Rahfeld, J. U. (1999) Identification and characterization of a 14 kDa human protein as a novel parvulin-like peptidyl prolyl cis/trans isomerase. *FEBS Lett*, 446, 278-282.

Uchida, T., Takamiya, M., Takahashi, M., Miyashita, H., Ikeda, H., Terada, T., Matsuo, Y., Shirouzu, M., Yokoyama, S., Fujimori, F. and Hunter, T. (2003) Pin1 and Par14 Peptidyl Prolyl Isomerase Inhibitors Block Cell Proliferation. *Chem. Biol*, 10, 15-24.

Vorherr, T. and Bannwarth, W. (1995) Phospho-serine and phospho-threonine building blocks for the synthesis of phosphorylated peptides by the Fmoc solid phase strategy. *Bioorg Med Chem Lett*, 5, 2661-2664.

Wang, Z., Wilson, G. F. and Griffith, L. C. (2002) Calcium/calmodulin-dependent protein kinase II phosphorylates and regulates the *Drosophila* egg potassium channel. *J Biol Chem*, 277, 24022-24029.

Weiwad, M., Küllertz, G., Schutkowski, M. and Fischer, G. (2000) Evidence that the substrate backbone conformation is critical to phosphorylation by p42 MAP kinase. *FEBS Lett*, 478, 39-42

Winkler, K. E., Swenson, K. I., Kornbluth, S, and Means, A. R. (2000) Requirement of the prolyl isomerase Pin1 for the replication checkpoint. *Science*, 287, 1644-1647.

Wintjens, R., Wieruszeski, J. M., Drobecq, H., Rousselot-Pailley, P., Buee, L., Lippens, G. and Landrieu, I. (2001) H-1 NMR study on the binding of Pin1 Trp-Trp domain with phosphothreonine peptides. *J Biol Chem*, 276, 25150-25156.

Wu, X., Wilcox, C. B., Devasahayam, G., Hackett, R. L., Arevalo-Rodriguez, M., Cardenas, M. E., Heitman, J. and Hanes, S. D. (2000) The Ess1 prolyl isomerase is linked to chromatin remodeling complexes and the general transcription machinery. *Embo J*, 19, 3727-3738.

Wulf, G. M., Ryo, A., Wulf, G. G., Lee, S. W., Niu, T., Petkova, V. and Lu, K. P. (2001) Pin1 is overexpressed in breast cancer and cooperates with Ras signaling in increasing the transcriptional activity of c-Jun towards cyclin D1. *Embo J*, 20, 3459-3472.

Yaffe, M. B., Schutkowski, M., Shen, M., Zhou, X. Z., Stukenberg, P. T., Rahifeld, J. U., Xu, J., Kuang, J., Kirschner, M. W., Fischer, G., Cantley, L. C. and Lu, K. P. (1997) Sequence-specific and phosphorylation-dependent proline isomerization: a potential mitotic regulatory mechanism. *Science*, 278, 1957-1960.

Yao, J. L., Kops, O., Lu, P. J. and Lu, K. P. (2001) Functional conservation of phosphorylation-specific prolyl isomerases in plants. *J Biol Chem*, 276, 13517-13523.

Zhang, Y., Fussel, S., Reimer, U., Schutkowski, M. and Fischer, G. (2002) Substrate-based design of reversible Pin1 inhibitors. *Biochemistry*, 41, 11868-11877.

Zhou, X. Z., Lu, P. J., Wulf, G., Lu, K. P. (1999) Phosphorylation-dependent prolyl isomerization: a novel signaling regulatory mechanism. *Cell Mol Life Sci*, 56, 788-806

Zhou, X. Z., Kops, O., Werner, A., Lu, P. J., Shen, M., Stoller, G., Küllertz, G., Stark, M., Fischer, G. and Lu, K. P. (2000) Pin1-dependent prolyl isomerization regulates dephosphorylation of Cdc25C and tau proteins. *Mol Cell*, 6, 873-883.

INCORPORATION BY REFERENCE

All publications, patent applications, patents, and other references mentioned herein are incorporated by reference. In addition, the materials, methods, and examples are illustrative only and not intended to be limiting.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A peptide capable of inhibiting the peptidyl prolyl isomerase activity of Pin1, or a Pin1-related enzyme, comprising the structure:

R-Xaa-Daa-Yaa-Zaa-Taa-S wherein
R is 0-5 amino acid residues;
S is 0-5 amino acid residues;
Daa is a threonine;
Zaa is any amino acid or amino acid analog;
Xaa, if present, is any amino acid or amino acid analog;
Taa, if present, is any amino acid, or amino acid analog; and
Yaa is a proline or proline analog.

2. The peptide of claim 1, wherein said threonine further comprises a negatively charged tetra or penta valent moiety.

3. The peptide of claim 2, wherein said negatively charged tetra or penta valent moiety is selected from the group consisting of —$OPO_3^{2-}$, —$PO_3^{2-}$, —$OSO_3^{2-}$, and $OBO_3^{2-}$.

4. The peptide of claim 1, wherein Taa is Gln, or a Gln analog.

5. The peptide of claim 1, wherein Xaa is a cyclic amino acid, or analog thereof.

6. The polypeptide of claim 5, wherein said cyclic amino acid is aromatic.

7. The polypeptide of claim 6, wherein said aromatic amino acid, or amino acid analog, comprises a sulfur.

8. The polypeptide of claim 7, wherein said aromatic amino acid, or amino acid analog, comprises a benzothiophene.

9. A peptide capable of inhibiting the peptidyl prolyl isomerase activity of Pin1, or a Pin1-related enzyme, comprising the structure:

R-Xaa-D-pSer-Yaa-Zaa-Taa-S wherein
pSer is a phosphoserine residue;
R is 0-5 amino acid residues;
S is 0-5 amino acid residues;
Zaa is any amino acid or amino acid analog;
Xaa, if present, is any amino acid or amino acid analog;
Taa is Gln, or a Gln analog; and
Yaa is a proline or proline analog.

10. The peptide of claim 9, wherein Xaa is an cyclic amino acid, or analog thereof.

11. The polypeptide of claim 10, wherein said cyclic amino acid is aromatic.

12. The polypeptide of claim 11, wherein said aromatic amino acid, or amino acid analog, comprises a sulfur.

13. The polypeptide of claim 12, wherein said aromatic amino acid, or amino acid analog, comprises a benzothiophene.

14. The peptide of claim 9, wherein Zaa is an aromatic amino acid or analog thereof.

15. A peptide capable of inhibiting the peptidyl prolyl isomerase activity of Pin1, or a Pin1-related enzyme, comprising the structure:

R-Xaa-D-pThr-Yaa-Zaa-Taa-S wherein
pThr is a phosphothreonine residue;
R is 0-5 amino acid residues;
S is 0-5 amino acid residues;
Zaa is any amino acid or amino acid analog;
Xaa, if present, is any amino acid or amino acid analog;
Taa, if present, is any amino acid, or amino acid analog; and
Yaa is a proline or proline analog.

16. The peptide of claim 15, wherein Taa is Gln, or a Gln analog.

17. The peptide of claim 15, wherein Xaa is an cyclic amino acid, or analog thereof.

18. The polypeptide of claim 17, wherein said cyclic amino acid is aromatic.

19. The polypeptide of claim 18, wherein said aromatic amino acid, or amino acid analog, comprises a sulfur.

20. The polypeptide of claim 19, wherein said aromatic amino acid, or amino acid analog, comprises a benzothiophene.

21. The peptide of claim 15, wherein Zaa is an aromatic amino acid or analog thereof.

22. The peptide of claim 15, wherein Xaa is an amino acid analog from the amino acid analogs presented in Table I.

23. The peptide of claim 15, wherein Zaa is an amino acid analog selected from the amino acid analogs presented in Table I.

24. The peptide of claim 15, wherein Yaa is an amino acid analog selected from the amino acid analogs presented in Table I.

25. The peptide of claim 20, wherein Xaa, Yaa, and Zaa are the residues identified in Table II.

26. A peptide comprising the structure Ac-Lys($N^\epsilon$-biotinoyl)-Ala-Ala-Bth-D-Thr($PO_3H_2$)-Pip-Nal-Gln-$NH_2$.

27. A peptide comprising the structure Ac-Phe-D-Thr($PO_3H_2$)-Pip-Nal-Gln-$NH_2$.

28. A pharmaceutical composition comprising the peptide of any one of claims 1, 9, or 15.

* * * * *

UNITED STATES PATENT AND TRADEMARK OFFICE
CERTIFICATE OF CORRECTION

| | | |
|---|---|---|
| PATENT NO. | : 8,258,099 B2 | Page 1 of 1 |
| APPLICATION NO. | : 11/632588 | |
| DATED | : September 4, 2012 | |
| INVENTOR(S) | : Kun Ping Lu et al. | |

It is certified that error appears in the above-identified patent and that said Letters Patent is hereby corrected as shown below:

In the Claims

Column 52, Line 1, replace "claim 20" with --claim 15--.

Signed and Sealed this
Twelfth Day of May, 2015

Michelle K. Lee
*Director of the United States Patent and Trademark Office*